(12) United States Patent
Joh

(10) Patent No.: US 12,396,881 B2
(45) Date of Patent: Aug. 26, 2025

(54) WEARABLE URINARY COLLECTION APPARATUS

(71) Applicant: William K. Joh, West Bloomfield, MI (US)

(72) Inventor: William K. Joh, West Bloomfield, MI (US)

( * ) Notice: Subject to any disclaimer, the term of this patent is extended or adjusted under 35 U.S.C. 154(b) by 0 days.

(21) Appl. No.: 19/042,647

(22) Filed: Jan. 31, 2025

(65) Prior Publication Data

US 2025/0177188 A1 Jun. 5, 2025

Related U.S. Application Data

(63) Continuation-in-part of application No. 18/107,726, filed on Feb. 9, 2023.

(60) Provisional application No. 63/732,736, filed on Sep. 17, 2024, provisional application No. 63/372,241, filed on Feb. 28, 2022.

(51) Int. Cl.
  *A61F 5/453* (2006.01)
  *A61F 5/44* (2006.01)

(52) U.S. Cl.
  CPC ............ *A61F 5/453* (2013.01); *A61F 5/4404* (2013.01)

(58) Field of Classification Search
  CPC ....................................................... A61F 5/453
  See application file for complete search history.

(56) References Cited

U.S. PATENT DOCUMENTS

| | | |
|---|---|---|
| 3,724,461 A | 4/1973 | Eisenberg |
| 3,822,720 A | 7/1974 | Souza |
| 4,022,213 A | 5/1977 | Stein |
| 4,239,044 A * | 12/1980 | Pavlinch ............... A61F 5/453 600/580 |
| 4,364,510 A | 12/1982 | Buchanan |
| 4,387,726 A | 6/1983 | Denard |
| 4,416,308 A | 11/1983 | Bower |
| 4,626,250 A | 12/1986 | Schneider |
| 4,994,051 A | 2/1991 | Walsh |

(Continued)

FOREIGN PATENT DOCUMENTS

| | | |
|---|---|---|
| CN | 215690284 U | 2/2022 |
| CN | 116531579 A | 8/2023 |

(Continued)

*Primary Examiner* — Susan S Su
*Assistant Examiner* — Erin A Kim
(74) *Attorney, Agent, or Firm* — Young Basile Hanlon & MacFarlane, P.C.

(57) ABSTRACT

A wearable urinary collection apparatus includes an inner collection member configured to receive at least a portion of a length of a penis of a user, a urine collection receptacle configured to collect urinary fluid therein, and a harness configured to support the urine collection receptacle relative to the user. The urine collection receptacle includes a redundant urine collection area formed from inverting a portion of the urine collection apparatus inward and configured to receive the urine collection receptacle. A contractile tube is disposed within the redundant urine collection area. When the inner collection member is received in the redundant urine collection area, a guide tube of the inner collection member extends through the contractile tube into the urine collection receptacle to define a fluid flow path from the inner collection member to the urine collection receptacle.

20 Claims, 20 Drawing Sheets

(56) References Cited

U.S. PATENT DOCUMENTS

| | | |
|---|---|---|
| 5,013,308 A | 5/1991 | Sullivan et al. |
| 5,067,821 A | 11/1991 | Young |
| 5,078,707 A | 1/1992 | Peter Klug |
| 5,084,037 A | 1/1992 | Barnett |
| 5,354,132 A | 10/1994 | Young et al. |
| 5,380,312 A * | 1/1995 | Goulter .................. A61F 5/453 |
| | | 604/352 |
| 6,116,780 A | 9/2000 | Young et al. |
| 6,223,751 B1 | 5/2001 | Park |
| 9,737,433 B2 | 8/2017 | Joh |
| 10,582,699 B1 | 3/2020 | Arthurs |
| 11,224,535 B2 | 1/2022 | Joh |
| 2008/0250554 A1 | 10/2008 | Smith |
| 2009/0062755 A1 | 3/2009 | Burgess et al. |
| 2010/0312203 A1 | 12/2010 | House |
| 2012/0238976 A1 | 9/2012 | Foster |
| 2013/0144271 A1 | 6/2013 | Passadore et al. |
| 2015/0080818 A1 | 3/2015 | Sekiyama et al. |
| 2017/0216081 A1 | 8/2017 | Accosta |
| 2019/0314189 A1 | 10/2019 | Acosta |
| 2019/0374373 A1 | 12/2019 | Joh |
| 2021/0228401 A1 | 7/2021 | Becker et al. |
| 2021/0401613 A1 | 12/2021 | Chiang |
| 2023/0020563 A1 | 1/2023 | Sharma et al. |

FOREIGN PATENT DOCUMENTS

| | | |
|---|---|---|
| JP | 2006326052 A | 12/2006 |
| WO | 2021026188 A1 | 2/2021 |

\* cited by examiner

WEARABLE URINARY COLLECTION APPARATUS

CROSS-REFERENCE TO RELATED APPLICATION(S)

This application is a continuation-in-part of U.S. application Ser. No. 18/107,726, filed on Feb. 9, 2023, which claims priority to and the benefit of U.S. Provisional Application No. 63/372,241, filed on Feb. 28, 2022. This application claims priority to and the benefit of U.S. Provisional Application No. 63/732,736, filed on Sep. 17, 2024. The contents of the foregoing applications are incorporated herein by reference in their entireties for all purposes.

TECHNICAL FIELD

The present disclosure relates to wearable urinary collection apparatuses, and more particularly, to ambulatory and stationary urinary collection apparatuses configured to inhibit backflow of urinary fluid collected therein.

BACKGROUND

There are many known apparatus for collecting voided urine resulting from incontinency. One type of the known apparatus is wearable adult size diapers having materials which absorb urine, and which are typically intended to be disposed of after a single use. Another type of the known apparatus includes some type of storage receptacle in which an individual's discharged urine is collected and stored, such that it may be disposed of when there is an opportunity to do so. The present disclosure pertains to this later type of the known apparatus.

The present inventor has previously proposed several different types of wearable urinary collection apparatuses having a urine collection receptacle, including those discussed in U.S. Pat. No. 11,224,535 to Joh (the '535 patent), the entire disclosure of which is incorporated herein by reference.

SUMMARY

One aspect of the present disclosure is a wearable urinary collection apparatus. The wearable urinary collection apparatus includes an elongate, tubular, flexible, collection receptacle which receives and stores urine therein. The collection receptacle also includes an entrance opening near one end thereof which is configured to receive a user's penis therethrough so that urine discharged from the user's penis will flow into the collection receptacle.

The collection receptacle also includes a constriction formed at an intermediate position of the collection receptacle. The constriction defines a constricted opening at the intermediate position that has a diameter smaller than an inner diameter of the collection receptacle. Accordingly, the urine which a user discharges into the collection receptacle must pass through the constricted opening to pass further inward of the collection receptacle from the constriction.

The wearable urinary collection apparatus also includes a tubular member that has opposite open ends and a diameter which is smaller than the inner diameter of the collection receptacle. The tubular member is shorter than the collection receptacle and has one of the opposite open ends thereof connected to the intermediate portion of the receptacle at the constriction in alignment with the constricted opening. Accordingly, the urine which passes through the constricted opening will pass into the tubular member.

The wearable urinary collection apparatus also includes a check valve provided at the one of the opposite open ends of the tubular member connected to the intermediate portion of the collection receptacle at the constriction. The check valve is configured to permit urine to freely pass from the constricted opening into the tubular member. The check valve is also configured to block urine from flowing from the tubular member into the constricted opening.

In some implementations, each of the collection receptacle, the small tubular member and the check valve are constructed of plastic sheet material. Furthermore, the check valve may include two flaps of plastic sheet material, in which the two flaps are provided on opposite sides of the constricted opening. Each of the flaps may extend inward of the tubular member by an axial length which is longer than a sum of the diameter of the constricted opening and a distance from the constricted opening to the flap. Furthermore, each of the flaps may have one end separately secured at the constriction and the axial length of each of the flaps is longer than a sum of the diameter of the constricted opening and a distance from the constricted opening to where the flap is secured at the constriction. Additionally, each of the flaps may be spaced inward of the constriction. Finally, the axial length by which one of the flaps extends inward of the tubular member is longer than the axial length by which the other of the flaps extends inward of the tubular member.

In some implementations, the wearable urinary collection apparatus further includes an expandable entrance opening provided at the entrance opening near the one end of the collection receptacle. The expandable entrance opening may be configured to receive the user's penis therethrough. Furthermore, the expandable entrance opening may include an elastic band that normally urges the expandable entrance opening to engage the user's penis.

In some implementations, the wearable urinary collection apparatus further includes a harness which is configured to be disposed about a user's waist. The harness may include at least one fastener configured to secure the collection receptacle to the front portion of the harness such that the user may insert the user's penis into the entrance opening of the collection receptacle. The harness may include a waist strap, a pair of supporting straps, and a bridge connection. The waist strap is configured to be worn about a user's waist. The pair of supporting straps each have opposite ends connected to the waist strap so that the supporting straps extend on opposite sides of the suer's pubic area. The bridge connection connects intermediate portions of the supporting straps at a level of the user's inferior pubic tubercle. The bridge connection may be 2-4 cm long and at least one fastener may be provided on at least one of the bridge connection portions of the supporting straps adjacent to the bridge connection.

In some implementations, the wearable urinary collection apparatus further includes a tubular supporting sleeve in which the collection receptacle may be disposed when the collection receptacle is being worn by the user. The tubular supporting sleeve may have an upper end which is open, and which is configured to surround the entrance opening of the collection receptacle when the collection receptacle is disposed in the tubular supporting sleeve. The tubular supporting sleeve may include at least one fastener at the upper end which is configured to secure the entrance opening of the tubular collection receptacle to the upper end. The at least one fastener at the first open end of the supporting sleeve may be configured to support the entrance opening of the tubular collection receptacle non-coaxially within the first open end of the supporting sleeve and to define an area of the first open end of the support sleeve adjacent to the entrance opening of the tubular collection receptacle through which the user may insert his scrotum into the tubular supporting sleeve. An opposite end of the tubular collection receptacle may have a closable opening provided therewith such that the opposite end of the tubular collection receptacle may be selectively opened or closed. The wearable urinary collection apparatus may further include an elongate, flexible member provided at the opposite end of the tubular collection receptacle which is configured to be gripped and moved by the user for manipulating the opposite end of the collection receptacle.

Another aspect of the present disclosure is a wearable urinary collection apparatus that includes an inner collection member, a urine collection receptacle, and a harness. The inner collection member is configured to receive at least a portion of a length of a penis of a user. The inner collection member extends from an upper end to a lower end. The inner collection member includes a voiding area disposed at the lower end of the inner collection member and a guide tube extending from the voiding area away from the upper end. The urine collection receptacle is configured to collect urinary fluid therein. The urine collection receptacle includes one or more mating features, a redundant urine collection area configured to receive the inner collection member, and a tubular port disposed in the redundant urine collection area. The harness is configured to support the urine collection receptacle relative to the user. The harness includes securing straps configured to extend around respective portions of the user. The harness also includes one or more complementary mating features extending along a portion of at least one of the securing straps. The one or more complementary mating features are couplable to the one or more mating features of the urine collection receptacle. When the inner collection member is received in the redundant urine collection area of the urine collection receptacle, the guide tube extends through the tubular port into the urine collection receptacle to define a fluid flow path from the inner collection member to the urine collection receptacle.

Another aspect of the present disclosure is a urinary collection system that includes an inner member and a membrane. The inner member is configured to extend around at least a portion of a penis. The inner member includes a guide tube that extends from an end portion of the inner member. The membrane is configured to collect urinary fluid therein. The membrane includes a redundant fluid collection portion that is configured to extend around at least a portion of the inner member. The redundant fluid collection portion includes a port. The guide tube of the inner member is configured to extend through the port of the membrane to seal the membrane at an interface between the guide tube and the port and to form a fluid flow path from the inner member into the membrane. The redundant urine collection portion is configured to collect the urinary fluid that leaks through the seal formed at the interface between the guide tube and the port.

Another aspect of the present disclosure is a method for affixing a wearable urinary collection apparatus to a user having a penis. The method includes inserting a length of the penis into an inner collection member. The inner collection member includes a penile sleeve configured to extend along a shaft of the penis, and a stream tube configured to be adjacent to a terminal end of the penis. The stream tube includes a flexible valve disposed at a terminal end thereof. The method also include inserting the flexible valve of the inner collection member through a contractile tube of a urine collection receptacle to dispose the flexible valve within the urine collection receptacle and to form a fluid flow path from the inner collection member into the urine collection receptacle. The urine collection receptacle is configured to collect urine therein. An interface between the stream tube and the contractile tube is configured to seal the urine collection receptacle. The method also includes inserting the inner collection member into a redundant collection area of the urine collection receptacle. The redundant collection area is configured to collect the urine that leaks through the interface between the stream tube and the contractile tube. The redundant collection area includes the contractile tube.

Another aspect of the present disclosure is a wearable urinary collection apparatus that includes an inner member, a tubular membrane configured to collect urinary fluid therein, and a harness. The inner tube member includes a stream guide tube disposed at an end portion of the inner member, in which the end portion of the inner member is configured to receive a penis glands of a penis of a user. The inner member also includes a sleeve portion extending from the end portion of the inner member and configured to extend over a shaft of the penis of the user. The tubular membrane includes an inverted portion formed from an upper end of the tubular membrane inverting inwards at an inversion such that the tubular membrane extends longitudinally from a lower end of the tubular membrane that is opposite the upper end to terminate at the inversion. The tubular membrane also includes a contractile stem tube disposed within the inverted portion and extending through the tubular membrane. The inverted portion is configured to receive the inner member such that the stream guide tube extends through the contractile stem tube to provide a fluid flow path into the tubular membrane from the inner member. The tubular membrane also includes a mating feature extending away from the tubular membrane. The harness includes a complementary mating feature releasably couplable to the mating feature of the tubular membrane. The harness is configured to support the membrane relative to the user such that the inversion of the tubular membrane is spaced from the user and the lower end of the tubular membrane extends away from the user.

DETAILED DESCRIPTION

Although the following disclosure offered for public dissemination is detailed to ensure adequacy and aid in understanding of the disclosed implementations, the following disclosure is not intended to prejudice that purpose of a patent which is to cover each new inventive concept therein no matter how it may later be disguised by variations in form or additions of further improvements. There have been chosen specific exemplary implementations of a urinary collection apparatus according to the present disclosure and specific alternative structures and modifications thereto. The exemplary implementations chosen for the purposes of illustration and description of the structures and methods described herein are shown in the accompanying drawings forming a part of the specification.

The advantages and features of the present disclosure will be readily apparent from the following detailed description. The present disclosure relates to a wearable urinary collection apparatus for use, for example, by an active individual with urinary incontinence issues. The wearable urinary collection apparatus described herein may be configured to be inconspicuously and comfortably worn by the individual to collect and safely store urine voided by the individual and may include means for preventing backflow and leakage. The wearable urinary collection apparatus described herein may be easy and cost efficient to manufacture. More particularly, the present disclosure pertains to such wearable urinary collection apparatuses which improve over conventional wearable urinary collection apparatuses, as well as methods of making the same.

As described previously, the present inventor has previously proposed several different types of wearable urinary collection apparatuses having a urine collection receptacle, including those discussed in U.S. Pat. No. 11,224,535 to Joh (the '535 patent). Each of these previously proposed apparatuses generally include a lightweight, tubular collection receptacle formed of thin plastic sheet material which is configured to receive and store urine therein and some type of backflow restricting/preventing means integrally provided with the collection receptacle. Some previously proposed apparatus also include means for conveniently and inconspicuously supporting the collection receptacle on an individual's body adjacent to the individual's penis such that the individual may readily void urine into the receptacle whenever the individual has need to do so.

Figure 1A:
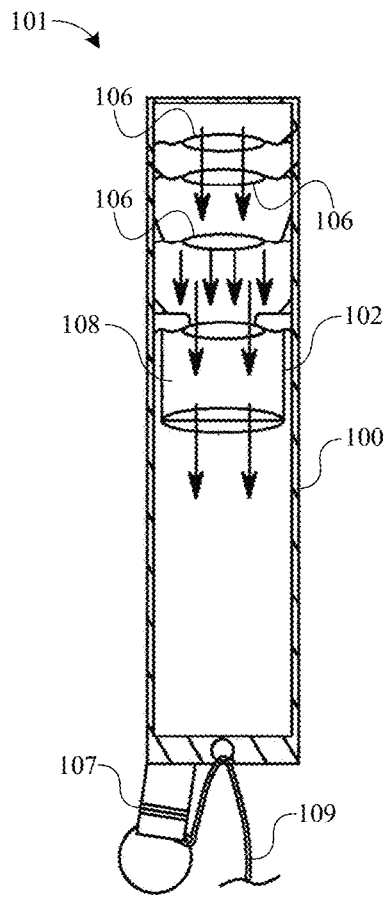
FIG. 1A is a side cross-sectional view illustration of an example of a known urinary collection apparatus previously proposed by the present inventor that includes a tubular entrance port provided near an entrance opening of a urine collection receptacle.
Figure 1B:
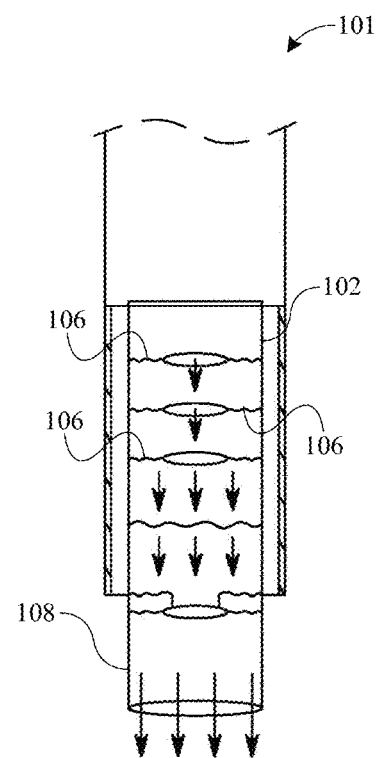
FIG. 1B is a side cross-section view illustration of the known urinary collection apparatus of FIG. 1A that depicts connections between the urine collection receptacle and the entrance opening for assembly thereof.
Figure 2A:
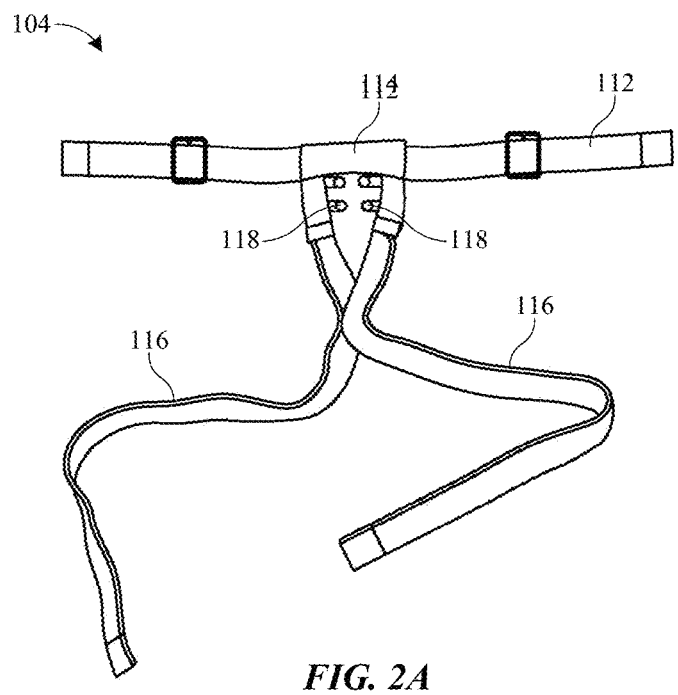
FIG. 2A is a front view illustration of an example of a known harness previously proposed by the present inventor that is configured to be secured around a waist of a user to support the urinary collection apparatus of FIG. 1A adjacent to a penis of the user.
Figure 2B:
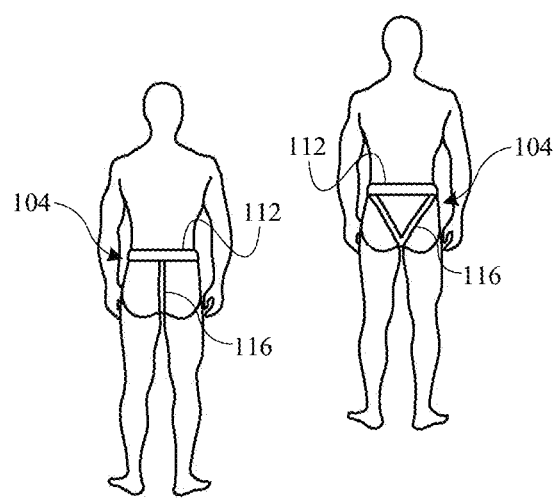
FIG. 2B includes rear view illustrations of examples of the known harness of FIG. 2A that depict a waist strap extending around the waist of the user and one or more securing straps extending from the waist strap around a buttocks of the user to support the urinary collection apparatus of FIG. 1A adjacent to the penis of the user.
Figure 3A:
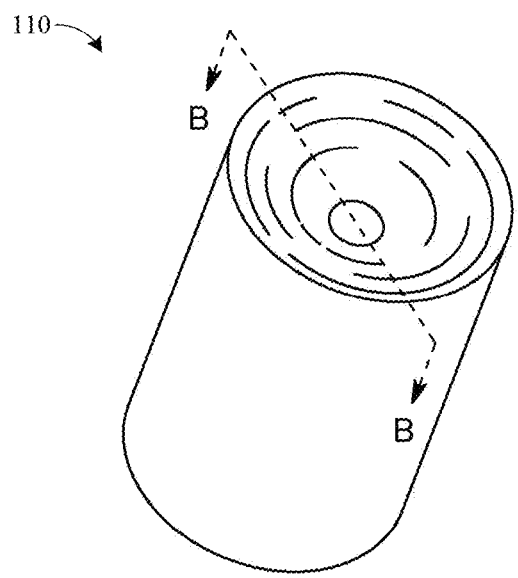
FIG. 3A is an upper perspective view illustration of a known elastomeric cap previously proposed by the present inventor that is configured to be secured around the penis or a penis glans of the user such that when the penis glans is inserted into the entrance port of the urinary collection apparatus of FIG. 1A, the known elastomeric cap prevents urine that is being discharged into the entrance port from leaking therefrom without causing discomfort to the user.
Figure 3B:
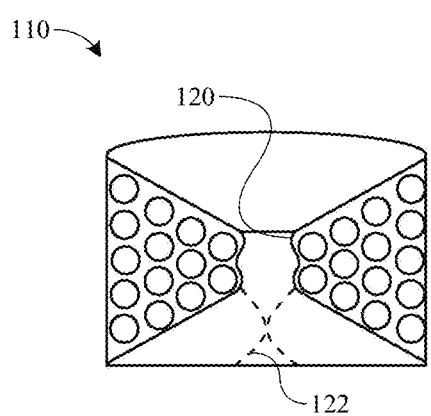
FIG. 3B is a side cross-sectional view illustration of the known elastomeric cap of FIG. 3A showing baffles that may further prevent urine that is being discharged into the entrance port from leaking therefrom without causing discomfort to the user.

FIGS. 1A-3B of the present disclosure correspond to some of the drawings in the '535 patent and depict the components of one of the present inventor's previously proposed urinary collection apparatuses. FIG. 1A depicts an example of a known wearable urinary collection apparatus 101 previously proposed by the present inventor that includes an elongate, tubular, urine collection receptacle 100 which may be 30 to 80 cm long and 8 to 12 cm wide and which integrally includes a backflow preventing means provided with an elongate, tubular entrance port 102 that is attached within the urine collection receptacle 100 at or near one end of the urine collection receptacle 100. FIG. 1B depicts a manner in which the structure of FIG. 1A is produced. FIGS. 2A-2B depict a harness 104 which is configured to be secured around a waist of the user and to support the urine collection receptacle 100 adjacent to a penis of the user so that a penis glans thereof may be readily inserted into and/or remain in the entrance port while the urine collection receptacle 100 extends downward from the harness 104 so that urine discharged from the penis flows down through the entrance port into the urine collection receptacle 100 to be collected. Finally, FIGS. 3A-3B depict an elastomeric cap 110 that may be secured around the user's penis or penis glans such that when the penis glans is inserted into the entrance port 102, the elastomeric cap prevents urine that is being discharged into the entrance port 102 from leaking out without causing discomfort to the user. FIG. 1A also depicts a lower portion of the urine collection receptacle 100 including a closable opening 107, which may be used to selectively empty any urine which has been collected in the urine collection receptacle 100, and an elongate cord 109 which is connected at a lower end of the urine collection receptacle 100, which may be used by an individual for manipulating the urine collection receptacle 100 when desired. While the discussion herein focuses on users having a penis, '535 patent also discloses an adapter which permits the urinary collection apparatus to be used by users that do not have a penis (e.g., users who have female sexual organs).

As disclosed in the '535 patent, the urine collection receptacle 100 and the entrance port 102 depicted in FIGS. 1A-1B may be formed of plastic sheet material, e.g., any suitable type of plastic, plastic-like, rubber, elastomeric, or polymeric material(s), which material(s) may possess or be treated to possess anti-bacterial properties, including very thin sheet materials such as latex, thermoplastic polyurethane (TPU), various types of polyethylene including high density polyethylene (HDPE), low density polyethylene (LDPE), etc. TPU sheet material is more stretchable and elastic than polyethylene sheet material and may be more suitable for use in the present disclosure as the increased stretchability and elasticity make the urine collection receptacle 100 more resistant to tearing and leaking, e.g., so that the urine collection receptacle 100 or portions thereof may reliably expand as urine is flows therein or as the urine collection receptacle 100 is moved, sat upon, or manipulated. The urine collection receptacle 100 and the entrance port 102 may be relatively inexpensive to construct from such material(s), so that they may be disposed of after a single use/wearing but are sufficiently durable that they may be cleaned and reused if desired. By constructing these components of plastic sheet material, they are desirably lightweight and tend to be flat when empty.

Such plastic sheet material components and/or portions thereof may be readily bonded together using only heat or energy pulses. This is a convenient and inexpensive means for securing the entrance port 102 within the one end of the urine collection receptacle 100 without unduly constricting urine flow through either the entrance port 102 or the urine collection receptacle 100.

According to an aspect of the known wearable urinary collection apparatus 101, and as shown in FIGS. 1A-1B, backflow preventing means are integrally provided with the entrance port 102 in the form of constrictions 106 that are formed by bonding opposing surfaces of the entrance port 102 together to significantly reduce the inner diameter ("ID") of the entrance port 102 at one or more locations along its length as the entrance port 102 extends into the urine collection receptacle 100, together with a so-called "flap" 108 which is an innermost portion of the entrance port 102 that extends inward of an innermost one of the constrictions 106. Again, these constrictions may be conveniently and inexpensively formed using only heat or energy pulses and may reduce the ID of the entrance port by 50% or more. The depicted implementation includes four such constrictions 106, which are aligned with each other at a center of the entrance port 102 in the width direction. However, as discussed in the '535 patent, the constrictions 106 may be provided in various numbers and in one or more shapes and sizes at various portions along the length of the entrance port 102.

While the entrance port 102 is securely fixed within the urine collection receptacle 100 as depicted in FIGS. 1A-1B, the innermost portion of the entrance port 102, provided inward of an inner most one of the constrictions 106, forms the flap 108, described above, which may move to some extent relative to the urine collection receptacle 100. As disclosed in the '535 patent, the flap 108 is particularly effective for preventing backflow of urine through the entrance port 102, especially when the flap 108 is used in combination with the constrictions 106. The opposing walls of the flap 108 will tend to remain engaged together other than when urine is flowing through the entrance port 102 into the main body and thereby prevents urine that has collected in the urine collection receptacle 100 from flowing back through the flap 108 even if some pressure is applied to the urine collection receptacle 100 when a user is active, sitting, or lying down. The inventor has determined that width and length of the flap 108 are important for achieving optimum backflow prevention, while assuring the ability of urine discharged by a user to surely to flow through the entrance port 102 into the urine collection receptacle 100.

For example, the inventor has determined that when the entrance port 102 including the flap 108 has a flat width of 8-9 cm and the flap 108 has an axial length of 4-6 cm extending inward of the urine collection receptacle 100 from the innermost one of the constrictions 106, which limits the ID of the flow path at the constriction to 2.5-4.0 cm, which is effective for preventing backflow of urine through the flap 108 and the entrance port 102 while permitting urine to surely flow through the entrance port 102 into the urine collection receptacle 100. Where the flap 108 length is shorter than 4.0 cm, it may not surely prevent backflow therethrough. Where the flap 108 length is more than 6.0 cm, it may simply require additional material without providing any better backflow prevention. The cord 109 shown in FIG. 1A desirably permits a user to manipulate the lower portion of the urine collection receptacle 100 when desired to prevent the urine collection receptacle 100 from interfering with the user's movements, e.g., the user may move the lower portion of the urine collection receptacle 100 and any urine contained therein to avoid the user sitting or lying on the urine collection receptacle 100 and applying significant pressure to the urine collection receptacle 100.

The harness 104 previously proposed by the inventor for supporting the urine collection receptacle 100 on a user's body is shown in FIGS. 2A-2B, with FIG. 2A depicting a perspective view of the harness 104 not attached to a user and FIG. 2B depicting manners in which the harness 104 may be worn by a user. Generally, the harness 104 includes an adjustable waist strap 112 which may be secured around a user's waist, a padded member 114 which is configured to extend downward from the waist strap 112 in front of a user's genital area and to have the urine collection receptacle 100 secured thereto, and a pair of securing straps 116, each of which has one end connected to a lower end of the padded member and an opposite free end which may be selectively secured to various portions of the waist strap 112 using an appropriate fastener, e.g., a hook-and-loop type fastener, a clip, a buckle, etc.

The waist strap 112 may be of any appropriate length, may include a fastener associated with free ends of the strap, e.g., a hook-and-loop type fastener, a clip, a buckle, etc., and may include means for adjusting the effective length of the waist strap 112. The waist strap 112 may be formed of any appropriate material that will not cause any discomfort to the user even if the harness is worn by the user for an extended length of time. For example, the waist strap 112 may be made of leather, fabric, elastic material, cushioning material, or a combination of two or more of these.

The padded member 114 may be shaped like an inverted U and provided to extend downward from the waist strap 112 in front of a user's genital area, including a first portion that extends parallel along a portion of the waist strap and a pair of opposing arms that extend at right angles to the first portion, and may have a size appropriate for covering the user's genital area, e.g., the first portion may be 8-12 cm long and 2-4 cm wide, and the arms may be 5-7 cm long and 2-4 cm wide. The padded member 114 may be formed of padded or cushioned material(s) that will not cause any discomfort or allergic reaction to a user and may be washed for reuse, e.g., fabric(s), foam covered fabric(s), etc. Additionally, the padded member 114 may be provided with securing means 118 for securing a urine collection receptacle (e.g., the urine collection receptacle 100) thereto, e.g., loops or hooks which are connected thereto and extend inward of the inverted U shape such that the entrance port 102 within the urine collection receptacle 100 may be conveniently disposed so that a user may readily insert his penis into the entrance port 102. The urine collection receptacle 100 and/or the entrance port 102 may be provided with straps (not shown) that may be tied or otherwise secured to the securing means 118 such that the entrance openings of these components are disposed directly in front of the user's genital area and such that the user may readily insert his penis into the entrance port 102 when desired.

The securing straps 116 of the harness may each generally comprise an elongate strip of material having one end secured to an end of one of the arms of the padded member 114 and having a fastener provided on the opposite end of the securing straps 116 for securing the end of the securing straps 116 to the waist strap 112, e.g., a hook-and-loop fastener, a clip, a button, etc., and intermediate portions of the securing straps 116 may be secured together with some type of fastener, e.g., thread which sews the straps together at the intermediate portions, a hook-and-loop fastener, a clip, etc. The material(s) used in forming the securing straps 116 may be the same as those used for making the waist strap 112 such as discussed above. As depicted in FIG. 2B, the securing straps 116 may be fastened to the waist strap 112 in various manners depending on the user's preference, e.g., the securing straps 116 may be arranged to fully overlap with each other and then may be extended between the user's legs adjacent to the user's genital area and having their free ends jointly fastened to the same portion of the waist strap 112, the free ends of the securing straps 116 may be extended through user's legs adjacent to the user's genital area and separately secured to different portions of the waist strap 112, etc.

Referring to FIGS. 3A-3B, FIG. 3A is a perspective view of the elastomeric cap 110 and FIG. 3B is a cross section of the elastomeric cap 110 along line B-B in FIG. 3A. The elastomeric cap 110 may be in the form of a cylindrical member constructed of soft flexible material such as a highly elastic polymer or polymer foam formed of silicone or other appropriate material which would be provided around a user's penis or penis glans so that when the penis glans is extended into the entrance port 102 the elastomeric cap 110 forms a leak-preventing seal with the inner surface of the entrance port 102. The elastomeric cap 110 may be generally cylindrical in shape with relatively thick walls of soft elastomeric material, with a central opening 120 extending axially therethrough and opposite end surfaces of the elastomeric cap 110 extending concave inward of the elastomeric cap 110. The diameter of the central opening 120 may be any appropriate size that will snugly engage the user's penis or penis glans when the cap is provided on the penis, but without causing any discomfort to the user. For example, the central opening 120 may have a diameter of 1-2 cm, noting that the highly elastic material of the elastomeric cap 110 will stretch to increase the size of the central opening 120 to fit the penis. If desired, a lubricant such as a hydrogel or the like may also be applied to surface(s) of the elastomeric cap 110, which is inserted into the entrance port 102 of the urine collection receptacle 100 to help prevent undesired backflow and seepage of urine. The degree of the concave shape of the opposite end surfaces of the elastomeric cap 110 may be such that in cross section the two sides of the elastomeric cap 110 extending from the central opening 120 appear like opposing isosceles triangles. With this shape, the elastomeric cap 110 will only engage a small portion of the user's penis but will provide a much larger surface area for engagement with the inner surface of the entrance port 102 of the urine collection receptacle 100 for preventing backflow and seepage.

As shown in FIG. 3B, the elastomeric cap 110 may also include a baffle 122 provided in association with a discharge end of the central opening 120. The baffle 122 may include flap(s) of a flexible plastic material, e.g., TPU, HDPE, LDPE, LLDPE, that extend from the end surface of the elastomeric cap 110 such that adjacent walls of the flaps will permit urine to flow downward therethrough, but which would otherwise remain engaged together or with the user's penis to prevent leakage of urine.

While such urinary collection apparatuses previously proposed by the present inventor functions appropriately, there remains a need in the art for the known devices to be improved on in several respects. For example, while some of the inventor's previously proposed apparatuses (e.g., the known wearable urinary collection apparatus 101 depicted in FIGS. 1A-3B) normally function very well to collect urine in the urine collection receptacle 100 and prevent urine from back flowing and/or otherwise leaking from the urine collection receptacle 100, the inventor has determined through experimental use of the previously proposed implementations that there may be some situations where the known wearable urinary collection apparatus 101 does not sufficiently prevent backflow and/or leakage of urine from the urine collection receptacle 100, particularly when the user is engaged in activities or when the individual is sitting or lying down and the urine collection receptacle 100 contains a relatively large amount of urine, e.g., eight or more fluid ounces. Furthermore, the previously proposed backflow preventing means may also unduly inhibit urine which is being discharged into the apparatus from freely and reliably flowing into the urine collection receptacle 100 of the known wearable urinary collection apparatus 101, which may result in leakage of the urine. Also, the previously proposed structures for supporting the urine collection receptacle 100 on an individual, including the harness 104 wearable about the individual's waist, could be improved in terms of reliability and convenience in use. Still further, the known wearable urinary collection apparatus 101 could be improved on in terms of conveniently preventing leakage of urine as it is being discharged into the urine collection receptacle 100 while also avoiding any discomfort to the individual.

Figure 4:
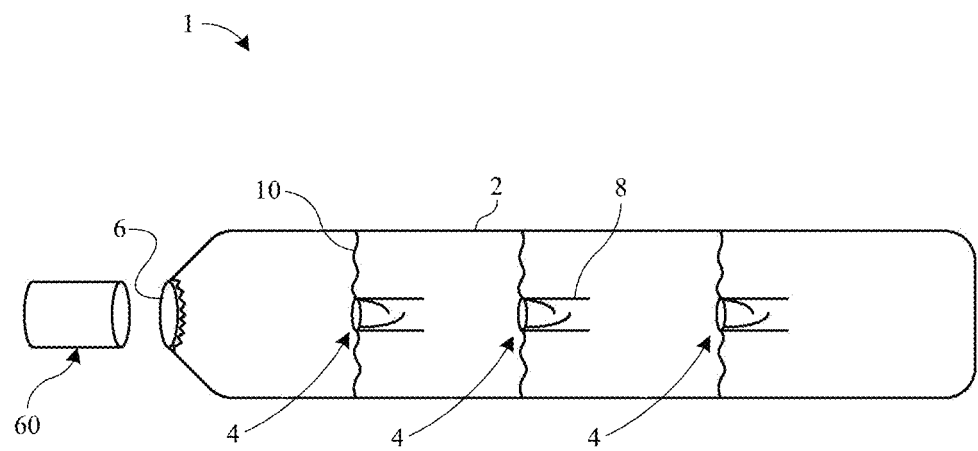
FIG. 4 is a side cross-sectional view illustration of an example of a urinary collection apparatus according to the present disclosure including a urine collection receptacle having backflow preventing means.

The present inventor has carefully studied the known apparatuses, such as those disclosed in the '535 patent (e.g., the known wearable urinary collection apparatus 101), and has performed substantial research regarding the discussed need and has discovered several improvements to the known apparatuses as discussed herein to arrive at an improved urinary collection apparatus. FIG. 4 is a cross-section view illustration of an example of a wearable urinary collection apparatus 1 according to the present disclosure. As shown, the wearable urinary collection apparatus 1 includes a urine collection receptacle 2 having backflow preventing means 4 disposed there-along. The wearable urinary collection apparatus 1 also includes an entrance opening 6 at one end thereof.

Figure 5A:
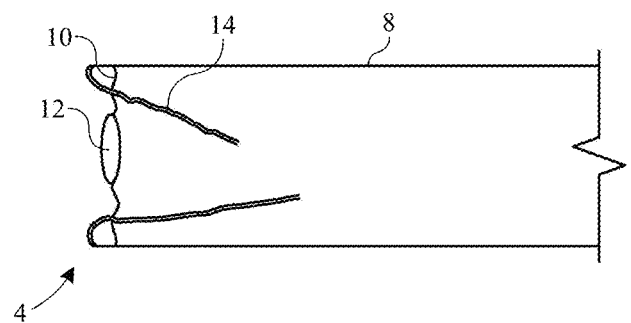
FIG. 5A is a side cross-sectional view illustration of the urinary collection apparatus of FIG. 4 showing a short tubular member of the backflow preventing means connected to the urine collection receptacle at a constriction formed at an intermediate portion of the urine collection receptacle and including a check valve formed from flaps.
Figure 5B:
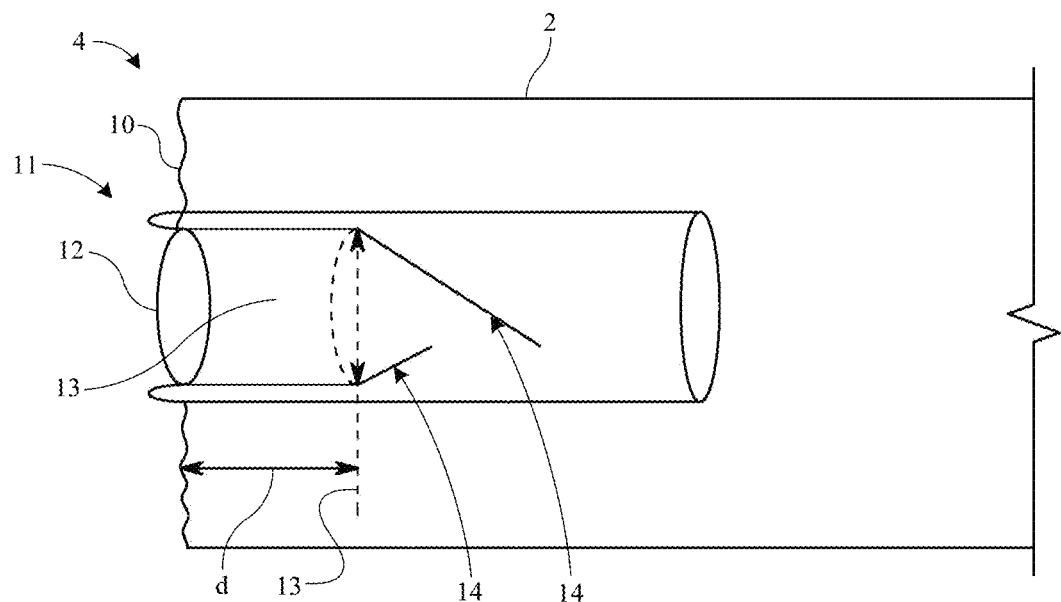
FIG. 5B is a side cross-sectional view illustration of the urinary collection apparatus of FIG. 4 showing another implementation of the backflow preventing means in which the flaps are spaced inwardly of the short tubular member from the constriction.
Figure 6:
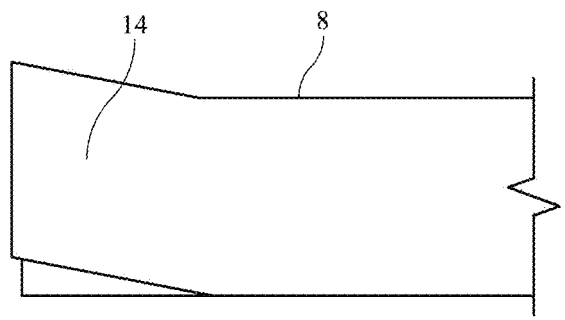
FIG. 6 is a side view illustration of the short tubular member of FIG. 4 before being attached to the urine collection receptacle.

Referring to FIGS. 4-6, the wearable urinary collection apparatus 1 is shown with integrated backflow prevention characteristics according to an exemplary implementation of the present disclosure. The wearable urinary collection apparatus 1 may generally comprise an elongate, tubular urine collection receptacle (e.g., the urine collection receptacle 2) which may be formed with the expandable entrance opening 6 at one end thereof and an opposite end which may be closed or which may include a closable opening and/or a manipulation cord such as the cord 109 previously proposed by the inventor and shown in present FIG. 1A, and a new, improved backflow preventing means (e.g., the backflow preventing means 4) integrally provided with the urine collection receptacle 2. The urine collection receptacle 2 may, for example, be 25-50 cm long and 8-15 cm wide, while the backflow preventing means 4 may include the smaller tubular member 8 which may be 6-9 cm long and 1.5-3 cm wide and connected within the urine collection receptacle 2 as discussed further herein. The wearable urinary collection apparatus 1 may also include the leakage preventing cap 60 which is simply fitted around the user's penis or penis glans, but not connected to the urine collection receptacle 2 or any other part of the wearable urinary collection apparatus 1, as discussed further herein.

The urine collection receptacle 2 and the backflow preventing means 4 may be formed of plastic sheet material, e.g., any suitable type of plastic, plastic-like, rubber, elastomeric, or polymeric material(s), which material(s) may possess or be treated to possess anti-bacterial properties, including very thin sheet materials such as latex, thermoplastic polyurethane (TPU), various types of polyethylene including high density polyethylene (HDPE), low density polyethylene (LDPE), etc. TPU sheet material is more stretchable and elastic than polyethylene sheet material, and may be more suitable for use in the present disclosure as the increased stretchability and elasticity make the urine collection receptacle 2 more resistant to tearing, and leaking, e.g., so that the receptacle or portions thereof may reliably expand as urine is flowed into it or as the urine collection receptacle 2 is moved, sat upon, or manipulated. The urine collection receptacle 2 and the backflow preventing means 4 may be relatively inexpensive to construct from such material(s), so that they may be disposed of after a single use/wearing but are sufficiently durable that they may be cleaned and reused if desired. Such plastic sheet material components and/or portions thereof may be readily bonded together using only heat or energy pulses, which is a convenient and inexpensive manner of bonding components together and for selectively forming constrictions in the components. By constructing these components of plastic sheet material they are desirably lightweight and tend to be flat when empty.

According to a first discovery, the inventor has determined that the entrance port 102 of the known wearable urinary collection apparatus 101, which was formed as a separate, elongate tubular member having the backflow preventing means integrally formed therewith and secured within one end portion of the urine collection receptacle 100, may not be necessary. Thus, the known wearable urinary collection apparatus 101 may be further simplified by eliminating the entrance port 102. Instead of the entrance port 102, the inventor has determined that a leakage inhibiting entrance opening—such as the expandable entrance opening 6—configured for receipt of a user's penis may be directly formed or attached at the one end portion of the urine collection receptacle 2 while a simpler and more reliable backflow preventing means—such as the backflow preventing means 4—may be provided integrally with the urine collection receptacle 2.

According to aspects of the present disclosure, the inventor has determined that an expandable leakage inhibiting entrance opening (e.g., the expandable entrance opening 6) for a user's penis or penis glans may be directly formed or attached at the one end portion of the urine collection receptacle 2 while the backflow preventing means 4 may have a simpler and more reliable structure than other backflow preventing means previously proposed by the inventor, such as the backflow preventing means included with the known wearable urinary collection apparatus 101 and (e.g., the entrance port 102) shown in present FIGS. 1A-1B.

Figure 7A:
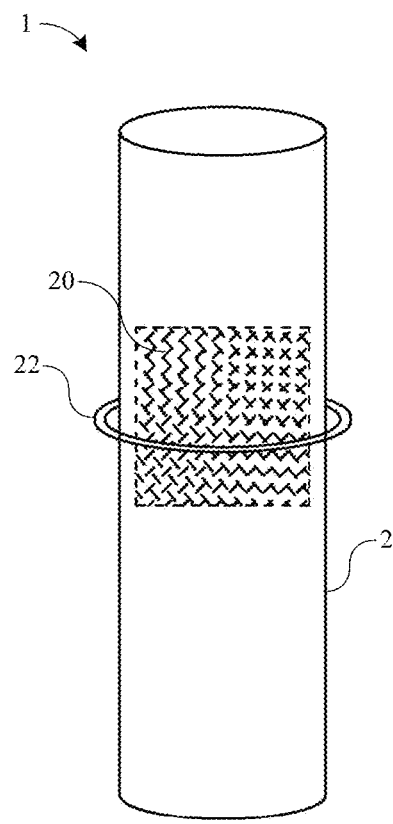
FIGS. 7A-7C are side view illustrations of the urinary collection apparatus of FIG. 4 demonstrating an example of a method for forming an expandable entrance opening one end of the urine collection receptacle according to the present disclosure, in which internal structures are shown using broken lines.
Figure 7B:
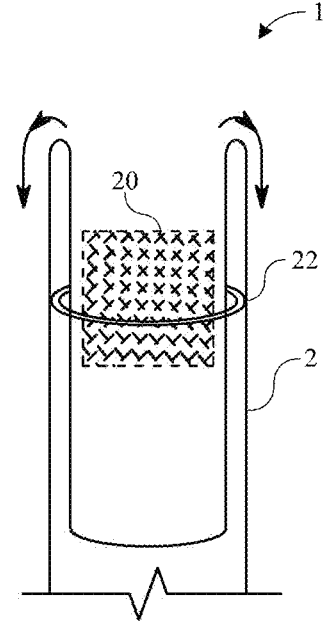
Figure 7C:
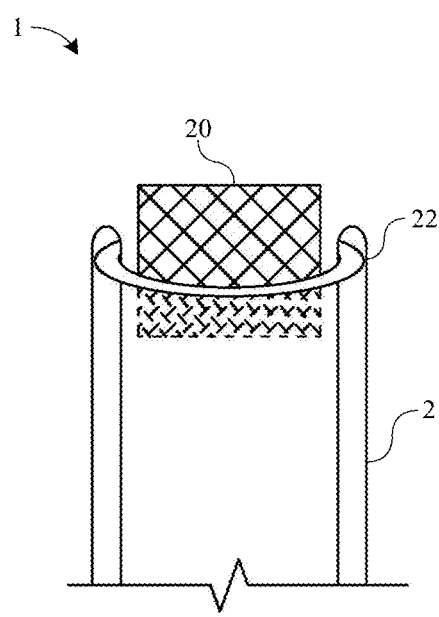

For example, referring to FIGS. 7A-7C, a leakage inhibiting entrance opening (e.g., the expandable entrance opening 6) may be easily formed at the one end portion of the urine collection receptacle 2 by, for example, inserting a thin, planar and somewhat rigid member 20 within one end portion of the urine collection receptacle 2, providing a small elastic band 22, e.g., a rubber band having a diameter of about 2 cm, around the portion of the urine collection receptacle 2 having the thin, planar and somewhat rigid member 20 therein so that the small elastic band 22 is near but spaced inward of one end of the urine collection receptacle 2, and then folding the one end of the urine collection receptacle 2 back over the small elastic band 22 and removing the thin, planar and somewhat rigid member 20 such that the small elastic band 22 is contained by the folded end portion of the urine collection receptacle 2 and is situated at a new end of the urine collection receptacle 2 to define the expandable entrance opening 6, which may be referred to as an expandable entrance opening. In this manner the small elastic band 22 and the fold of the plastic sheet material forming the urine collection receptacle 2 in which the small elastic band 22 is contained may become constricted, though easily expandable such that a user may directly insert his penis or penis glans therein. The elastic, expandable nature of the expandable entrance opening 6 as provided by the small elastic band 22 and stretchable plastic sheet material is advantageous for engaging the penis or penis glans with a small force sufficient to prevent urine which is being discharged by the penis from leaking out of the expandable entrance opening 6, but without causing discomfort to the user's penis. If desired, a lubricant such as a hydrogel or the like may also be applied to surface(s) of the user's penis or penis glans before it is inserted into the expandable entrance opening 6 to help prevent undesired seepage of urine and enhanced comfort. Also, while the expandable entrance opening 6 may be directly formed at one end of the urine collection receptacle 2, in some implementations, it may be formed as a separate tubular member of plastic sheet material which is attached at one open end of the urine collection receptacle 2 using heat or energy pulses.

Referring back to FIGS. 4-6, the backflow preventing 4 means may include a constriction 10 formed in the urine collection receptacle 2 which reduces (e.g., significantly reduces) the ID of the urine collection receptacle 2 at the position of the constriction 10 so that urine discharged into the urine collection receptacle 2 through the expandable entrance opening 6 will flow downward through the constriction 10 for being collected in the urine collection receptacle 2. The backflow preventing means 4 may also include a small tubular member 8, e.g., 6.0-9.0 cm long and 1.5-3.0 cm wide, having open opposite ends and formed of plastic sheet material, which has one of its open ends secured to the urine collection receptacle 2 at the constriction 10 such that urine which passes through the constriction 10 will also flow through the small tubular member 8. Finally, the backflow preventing means 4 may include a check valve 14 also formed of plastic sheet material provided at the one end of the tubular member 8 which is secured to the urine collection receptacle 2 at the constriction 10. The check valve 14 permits urine to freely pass further inward of the urine collection receptacle 2 through the small tubular member 8, but blocks the urine from passing back up through the small tubular member 8 and the constriction 10.

As described, the backflow preventing means 4 may include the constriction 10 formed widthwise in the urine collection receptacle 2 which significantly reduces the ID of the urine collection receptacle 2 at the position of the constriction 10 to an opening (e.g., the constricted opening 12) having an ID which may be ⅓ to ⅕ of the ID of the urine collection receptacle 2 where the urine collection receptacle 2 is free from the constriction 10. Stated differently, the constriction 10 may define the constricted opening 12 extending therethrough. Accordingly, urine discharged in the urine collection receptacle 2 though the expandable entrance opening 6 will flow downward through the constriction 10 before being collected in the urine collection receptacle 2. The small tubular member 8 has open opposite ends, one of which may be secured to the urine collection receptacle 2 at the constriction 10 such that urine which passes through the constricted opening 12 will also flow through the small tubular member 8. The check valve 14, also formed of plastic sheet material, provided at the one end of the tubular member 8 is secured to the urine collection receptacle 2 at the constriction 10. The check valve 14 permits urine to freely pass further inward of the urine collection receptacle 2 through the small tubular member 8, but blocks the urine from passing back up through the small tubular member 8 and the constriction 10.

The small tubular member 8 may be readily formed of plastic sheet material which is fixed into a tubular shape using heat of energy pulses similarly to the urine collection receptacle 2. While the ID of the small tubular member 8 may be 1.5-3.0 cm, the inventor has found that the bore or lumen of the small tubular member 8 is preferably ≤2.0 cm particularly at the end connected at the constriction 10. The plastic sheet material may be the same plastic sheet material used for forming the urine collection receptacle 2 but may be formed from a different plastic sheet material and/or may have a different thickness than the material used to form the urine collection receptacle 2. Again, TPU sheet material is preferred for forming each of these components because of its advantageous characteristics discussed herein. However, even if made of the same plastic material as that of the urine collection receptacle 2, the small tubular member 8 may have a smaller wall thickness than the urine collection receptacle 2 because it is not required to contain any urine therein, unlike the urine collection receptacle 2, and will remain in a substantially flat or collapsed state at all times, including when urine discharged by a user is passing therethrough. For example, the urine collection receptacle 2 may have a wall thickness of 0.025-0.150 mm (1-6 mil), while the small tubular member 8 and the check valve 14 may have a wall thickness of 0.025-0.075 mm (1-3 mil).

As described, the small tubular member 8 may be readily formed of plastic sheet material which is fixed into a tubular shape using heat of energy pulses similarly to the urine collection receptacle 2. While the ID of the small tubular member 8 may be 1.5-3 cm, the inventor has found that the bore or lumen of the member is preferably ≤2.0 cm particularly at the end connected at the constriction 10. The plastic sheet material may be the same plastic sheet material used for forming the urine collection receptacle 2 but may be a different plastic sheet material and/or may have a different thickness than the material used in forming the urine collection receptacle 2. Again, TPU sheet material is preferred for forming components of the wearable urinary collection apparatus 1 because of its advantageous characteristics discussed herein. However, even if made of the same plastic material as the urine collection receptacle 2, the small tubular member 8 may have a smaller wall thickness than the urine collection receptacle 2 because it is not required to contain any urine therein, unlike the urine collection receptacle 2, and will remain substantially flat or collapsed state at all times, including when urine discharged by a user is passing therethrough. For example, the urine collection receptacle 2 may have a wall thickness of 0.025-0.150 mm (1-6 mil), while the small tubular member 8 and the check valve 14 may have a wall thickness of 0.025-0.075 mm (1-3 mil).

Referring to FIGS. 4 and 7A-7C, the expandable entrance opening 6 may, for example, be easily formed at the one end portion of the collection receptacle 2 in a manner as shown in FIGS. 7A to 7C. Initially, the thin, planar and somewhat rigid member 20 may be inserted within one end portion of the urine collection receptacle 2, but spaced away from the an end opening of the urine collection receptacle 2, and a small, thin gauge elastic band, such as the small elastic band 22, e.g., a rubber band having a diameter of about 2 cm and thickness of 0.5-1.5 mm, may be provided around the portion of the urine collection receptacle 2 having the thin, planar and somewhat rigid member 20 therein so that the small elastic band 22 is near but spaced inward of one end of the urine collection receptacle 2 as shown in FIG. 7A. Then, the one end of the urine collection receptacle 2 may be folded back over the small elastic band 22 as shown in FIGS. 7B-7C. The thin, planar and somewhat rigid member 20 may then be removed from the urine collection receptacle 2 such that the small elastic band 22 is contained by the folded end portion of the urine collection receptacle 2 and is situated at a new end of the urine collection receptacle 2 to define the expandable entrance opening 6 shown in FIG. 4. In this manner, the small elastic band 22 and the fold of the plastic sheet material forming the urine collection receptacle 2 in which the small elastic band 22 is contained form the constricted, but easily expandable entrance opening (e.g., the expandable entrance opening 6) of the urine collection receptacle 2 into which a user may directly insert his penis or penis glans. The elastic, expandable nature of the expandable entrance opening 6 as provided by the small elastic band 22 and stretchable plastic sheet material is advantageous for engaging the penis or penis glans with a small force sufficient to prevent urine which is being discharged by the penis from leaking out of the expandable entrance opening 6, but without causing discomfort to the user's penis. If desired, a lubricant such as a hydrogel or the like may also be applied to surface(s) of the user's penis or penis glans before it is inserted into the expandable entrance opening 6 to help prevent undesired seepage of urine and enhanced comfort.

Figure 8:
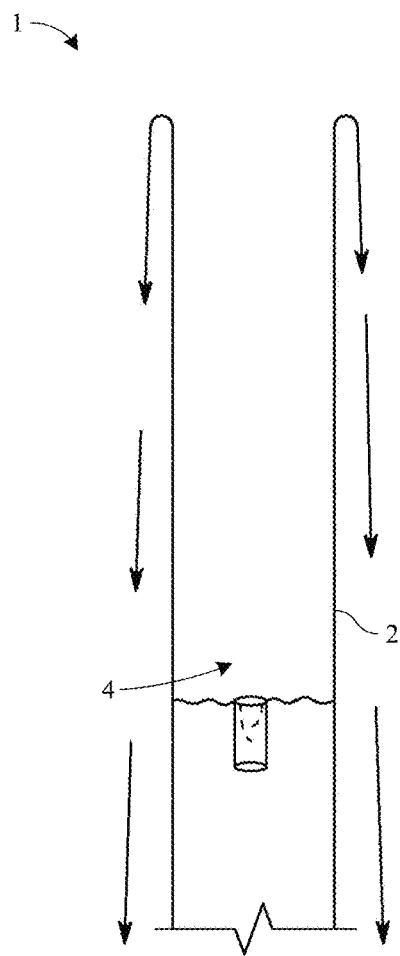
FIGS. 8-11 are side view illustrations of the urinary collection apparatus of FIG. 4 demonstrating a method for assembling the backflow preventing means with the urine collection receptacle according to the present disclosure.
Figure 9:
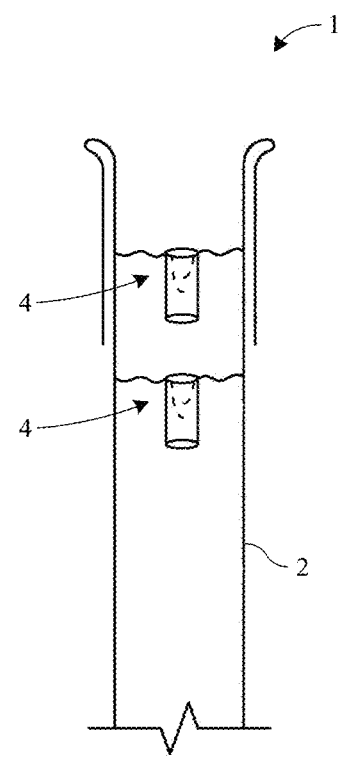

Also, while the expandable entrance opening 6 may be directly formed at one end of the urine collection receptacle 2, the expandable entrance opening 6 may be formed as a separate tubular member of plastic sheet material which is attached at one open end of the urine collection receptacle 2 using heat or energy pulses. Referring to FIGS. 8-11, for example, there is shown another example of the wearable urinary collection apparatus 1 according to an implementation of the present disclosure. Referring to FIG. 8, one open end of the urine collection receptacle 2 is folded back over an intermediate portion of the urine collection receptacle 2 and a first of the backflow preventing means 4, including the constricted opening 12, the small tubular member 8 and the check valve 14 is provided at one axially inward position along the urine collection receptacle 2. Referring to FIG. 9, a part of the one end of the urine collection receptacle 2 that had been folded over is moved back toward its original position and a second of the backflow preventing means 4, including another of the constricted opening 12, another of the small tubular member 8, and the check valve 14 is provided at another position along the urine collection receptacle 2 which is less axially inward than the position of the first of the backflow preventing means 4. At this time, the remaining folded portion of the one end of the urine collection receptacle 2 extends axially away from the second of the backflow preventing means 4 and defines a new open end of the urine collection receptacle 2. The new open end may extend out slightly in a lateral direction from the rest of the urine collection receptacle 2, and this is shown in a somewhat exaggeratedly large shape in FIG. 9. Such new end of the urine collection receptacle 2, including folded layers of the plastic sheet material, has enhanced strength compared to other portions of the urine collection receptacle 2 which include only a single layer of the plastic sheet material, and may be useful for supporting the urine collection receptacle 2 on a user's body through a harness, such as the harness 40 shown in FIG. 12 and/or a supporting sleeve, such as the supporting sleeve 50 shown in FIG. 13, as discussed further herein.

Figure 10:
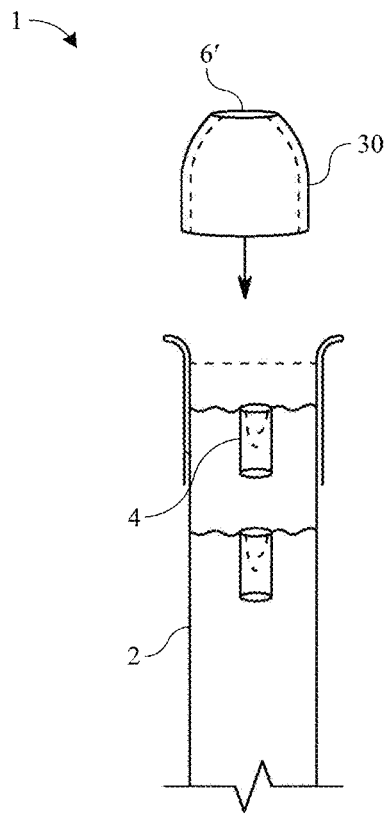

In FIG. 10 an example of the expandable entrance opening 6' that is not formed directly into the one end of the urine collection receptacle 2, as is done in the implementation of FIGS. 4 and 7A-7C, but rather the expandable entrance opening 6' is initially provided in a separate member 30, which is formed of plastic sheet material such as used in forming the urine collection receptacle 2, and then the separate member 30 is attached to the urine collection receptacle 2 at its one open end using heat, energy pulses, adhesive or other appropriate means.

The check valve 14 (e.g., forming part of the backflow preventing means 4) is a particularly important aspect of the present disclosure. As best shown in FIGS. 5A-5B, the check valve 14 may be provided in the form of two, separate flaps of plastic sheet material which may each have one end secured at the constriction 10 formed in the urine collection receptacle 2 which significantly reduces the ID of the urine collection receptacle 2 leading into the small tubular member 8 such that the flaps freely extend into the one connected end of the small tubular member 8, with the flaps being respectively disposed on opposite sides of a constricted opening 12 defined by the constriction 10. The flaps function as the check valve 14 because when a user discharges urine into the urine collection receptacle 2 (e.g., via the expandable entrance opening 6), the urine will readily pass through the constricted opening 12 and between the flaps into the small tubular member 8, but in the event of urine backflowing up through the small tubular member 8 for any reason, the flaps will tend to fold over the constricted opening 12 to block the backflowing urine from passing back out of the small tubular member 8 and through the constricted opening 12.

As described, the check valve 14 forming part of the backflow preventing means 4 is a particularly important aspect of the present disclosure. As shown in FIG. 5A, the check valve 14 may be provided in the form of two, separate flaps of plastic sheet material which may each have one end secured at the constriction 10 formed in the urine collection receptacle 2 such that the two flaps freely extend into the one connected end of the small tubular member 8 from the constriction 10, with the two flaps being respectively disposed on opposite sides of the constricted opening 12. The flaps function as the check valve 14 because when a user discharges urine into the expandable entrance opening 6, the urine will readily pass downward through the constricted opening 12 and between the two flaps into the small tubular member 8, but in the event of urine backflowing up through the small tubular member 8 for any reason, both flaps will tend to fold over the constricted opening 12 to block the backflowing urine from passing back out of the small tubular member 8 and through the constricted opening 12.

Referring to FIG. 5B, another implementation of the small tubular member 8 is shown. The small tubular member 8 shown in FIG. 5B is similar to the small tubular member shown in FIG. 5A. However, in the implementation shown in FIG. 5B, the attachment position of the end portion of the small tubular member 8 at the constriction 10 is different from the attachment position of the end portion of the small tubular member 8 shown in FIG. 5A such that the two flaps forming the check valve 14 are fully disposed within the one end of the small tubular member 8 and spaced away from the constriction 10 by a distance d. In other words, ends of the slits cut into the one end of the small tubular member 8 to define the flaps of the check valve 14 end at the position 13 and are spaced away from the constriction by the distance d. With the check valve 14 shown in FIG. 5B, a portion of the one end of the small tubular member 8 extends inward of the small tubular member 8 by the distance d, while the flaps of the check valve 14 extend further inward of the small tubular member 8 from the position 13. As with the implementation shown in FIG. 5A, each of the flaps of the check valve 14 should have sufficient axial length to fully cover the constricted opening 12, while one of the flaps may have a greater axial length than that of the other flap.

The flaps may be formed of the same plastic sheet material as used in forming the small tubular member 8 and may be conveniently and inexpensively formed integrally with the small tubular member 8. For example, the flaps may initially be provided as one end of the small tubular member 8, and two opposing slits may be formed in the one end portion of the tubular member 8 so as to define the flaps. Then, the flaps may be folded inward of the one end of the tubular member 8, and when the one end of the small tubular member 8 is attached at the constriction 10, the flaps may also be secured at different parts of the constriction 10. The flaps may be rectangular, square or some other shape, and may have different lengths, but each of the flaps should be sufficiently long such that when it is folded in the direction of the constricted opening 12, it may fully cover the constricted opening 12. For example, if the constricted opening 12 of the urine collection receptacle 2 at which the small tubular member 8 is attached is 1 cm in diameter and each of the flaps is connected to the constriction 10 0.5 cm away from the constricted opening 12, each of the flaps should have a length of at least 1.6 cm. If the flaps have different lengths, e.g., one is 0.2-0.5 cm longer than the other, in the event of urine backflowing up through the small tubular opening 8, the shorter of the flaps will tend to fold over the constricted opening 12 first and the longer of the flaps will then tend to fold over the shorter of the flaps.

As described, the flaps of the check valve 14 may be formed of the same plastic sheet material as used in forming the small tubular member 8, and may be conveniently and inexpensively formed integrally with the small tubular member. Referring to FIG. 6, for example, the two flaps may initially be provided as one end of the small tubular member 8 by forming two opposing slits in the one end portion of the tubular member 8 in an axial direction of the small tubular member 8 so as to define the flaps. Thereafter, the two flaps may be folded inward of the one end of the small tubular member 8, and when the one end of the small tubular member 8 is attached at the constricted opening 12, the two flaps may also be secured at different parts of the constriction 10 on opposite sides of the constricted opening 12. Each of the two flaps may have a curved shape corresponding to about half of the small tubular member 8, but the flaps may be rectangular, square or some other shape, and may have different axial lengths so that they extend inward of the small tubular member 8 by different the different lengths. However, each flap should be sufficiently long such that when it is folded in the direction of the constricted opening 12 it may fully cover the constricted opening 12. For example, if the constricted opening 12 is 1 cm in diameter and each of the flaps is connected at the constriction 10 about 0.5 cm away from the constricted opening 12, each flap should have a length of at least 1.6 cm. If the two flaps have different lengths, e.g., one is 0.2 to 0.5 cm longer than the other, in the event of urine backflowing up through the small tubular member 8, the shorter flap will tend to fold over the constricted opening 12 first and the longer flap will then tend to fold over the shorter flap. The rounded edges of the constricted opening 12 where the small tubular member is connected at the constriction 10 help to prevent the constricted opening 12 from closing when a user has discharged urine into the urine collection receptacle 2 and the urine flows inward of the urine collection receptacle 2 through the constricted opening 12 before being collected in the urine collection receptacle 2.

While backflow preventing means according to the present disclosure may comprise a single constriction 10 and single tubular member 8 having the check valve 14 at one end, as shown in FIG. 4, it is possible to provide a plurality of the constrictions 10 formed in spaced positions from each other along the urine collection receptacle 2, and a plurality of the small tubular members 8 and check valves 14 provided with the constrictions 10, respectively. For example, each of the constrictions 10 may be provided at the lateral center of the urine collection receptacle 2 and spaced from each other by 7-10 cm along the length of the urine collection receptacle 2, with one of the small tubular members 8 and one of the check valves 14 provided at each of the constrictions 10. The inventor has determined through experimentation that two of the constrictions 10, each having one of the small tubular members 8 and one of the check valves 14 provided therewith, is very effective at preventing any backflow, even when the urine collection receptacle 2 contains a relatively large amount of urine, e.g. ≥8 fluids ounces.

As described, while the wearable urinary collection apparatus 1 according to the present disclosure may include a single one of the backflow preventing means 4 comprising the constriction 10, the small tubular member 8, and the check valve 14, it is possible to provide a plurality of the backflow preventing means 4 provided in spaced positions from each other along the urine collection receptacle 2. For example, each of the backflow preventing means 4 may be provided at the lateral center of the urine collection receptacle 2 and spaced from each other by 7-10 cm along the length of the urine collection receptacle 2. The inventor has determined through experimentation that two of the backflow preventing means 4—each having one of the constrictions 10, one of the small tubular members 8, and one of the check valves 14 provided therewith—is very effective at preventing any backflow, even when the collection receptacle contains a relatively large amount of urine, e.g. 28 fluids ounces.

Additionally, the inventor has determined that if a manipulation cord or other member is provided at a lower end the urine collection receptacle 2, such as the cord 109 shown in FIG. 1A, the cord may be easily used to manipulate the lower portion of the urine collection receptacle 2 relative to the backflow preventing means 4 to further assure positively all backflow of urine out of the urine collection receptacle 2 is prevented. For example, the inventor has determined that if the cord is used to fold the lower portion of the urine collection receptacle 2 relative to an intermediate portion of the urine collection receptacle 2 inward of the backflow preventing means 4, the combination of the folded lower portion of the urine collection receptacle 2 and the backflow preventing means 4 is very effective for assuring that no backflow will occur.

As described, the inventor has determined that if a manipulation cord is provided at a lower end the collection receptacle 2, such as the cord 109 shown in FIG. 1A, the cord may be used to easily manipulate the lower portion of relative to the backflow preventing means 4 to further assure that positively any backflow of urine in the urine collection receptacle 2 is prevented. For example, the inventor has determined that if the cord 109 is used to fold the lower portion of the urine collection receptacle 2 relative to an intermediate portion of the urine collection receptacle 2 that is positioned inward of the backflow preventing means 4, the combination of the folded lower portion of the urine collection receptacle 2 and the backflow preventing means 5 is very effective for assuring that no backflow will occur from the urine collection receptacle 2 back up through the backflow preventing means 4.

Figure 12:
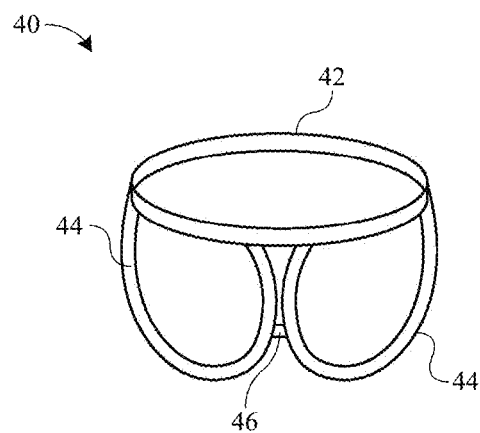
FIG. 12 is an upper perspective view illustration of an example of a harness according to the present disclosure that is configured to support the urine collection receptacle of the FIG. 4 adjacent to the penis of the user.

According to a second discovery, the inventor has determined that the harness 104 disclosed in the '535 patent and duplicated in present FIG. 2A may not always hold the known wearable urinary collection apparatus 101 at a position sufficiently close to a user's pubic area to permit the user to easily discharge urine into the urine collection receptacle 100 at all times. After considerable research, the inventor has developed an improved implementation of a harness 40 for supporting the urine collection receptacle 2 for consistent convenience in use. Referring to FIG. 12, the harness 40 includes a waist strap 42 that may be secured about a user's waist, a pair of supporting straps 44 that have opposite ends connected to different parts of the waist strap 42 such that portions of the supporting straps 44 extend on opposite sides of the user's pubic area, and a short, e.g., 2-4 cm, bridge connection 46 that connects intermediate portions of the supporting straps 44 at a level of the user's inferior pubic tubercle. The harness 40 defines a substantially triangular area between the waist strap 42, portions of the supporting straps 44 that extend from the waist strap 42, and the bridge connection 46, such that the substantially triangular area closely surrounds the user's pubic area. The inventor has determined that if the urine collection receptacle 2 is secured to the harness 40 such that the expandable entrance opening 6 of the urine collection receptacle 2 is supported by the supporting straps 44 close to the bridge connection 46, the user may easily discharge urine in the urine collection receptacle 2 at all times.

As described, the inventor has determined that the harness 104 disclosed in the '535 patent and duplicated in present FIGS. 3A-3B may not always hold an elongate, tubular collection receptacle, such as the urine collection receptacle 2, at a position sufficiently close to a user's pubic area to permit the user to easily discharge urine in the urine collection receptacle 2 at all times. After considerable research, the inventor has conceived of an improved harness for supporting an elongate, tubular collection receptacle such as the urine collection receptacle 2 for consistent convenience in use. Referring to FIG. 4, the harness 40 in includes the waist strap 42 that may be secured about a user's waist, a pair of supporting straps 44 that have opposite ends connected to different parts of the waist strap 42 such that when a user wears the harness 40, portions of the supporting straps 44 extend on opposite sides of the user's pubic area, and a short, e.g., 2-4 cm, bridge connection (e.g., the bridge connection 46) that connects intermediate portions of the securing straps 116 at a level of the user's inferior pubic tubercle. The harness 40 defines a substantially triangular area between the waist strap 42, portions of the supporting straps 44 that extend from the waist strap 42, and the bridge connection 46, such that the substantially triangular area closely surrounds the user's pubic area. The inventor has determined that if the urine collection receptacle 2 is secured to the harness 40 such that the expandable entrance opening 6 of the urine collection receptacle 2 is supported by the supporting straps 44 and/or the bridge connection 46, the user may be enabled to easily discharge urine into the urine collection receptacle 2 at all times.

Again, while the urinary collection apparatus 1 has been discussed as being used by male persons, it may also be used by females, and this typically involves use of an adapter. Appropriate adapters have been previously proposed by the present inventor in the '535 patent, e.g., see FIGS. 3A-3E of the '535 patent, and such adapters may be used together with the wearable urinary collection apparatus 1 according to the exemplary implementation of the present disclosure. The inventor has determined that the harness 40 may also be used by females, but for such use it may be desirable to modify the harness 40 by addition of a second short bridge connection (not shown) which is the same or similar to the bridge connection 46. The second short bridge connection may also be connected to the supporting straps 44 such that it extends in parallel to the bridge connection 46 but spaced away from the bridge connection by about 2-4 cm. With such modified harness including the second short bridge connection, a discharge end of the female adapter may be extended between the two short connections and into the expandable entrance opening 6 of the urine collection receptacle 2.

The urine collection receptacle 2 may be directly supported by the harness 40, e.g., by securing an edge of the urine collection receptacle 2 which surrounds the expandable entrance opening 6 in FIG. 10 to the supporting straps 44 and/or the bridge connection 46 using any appropriate fastening means. The inventor has determined that if the expandable entrance opening 6 is disposed closely adjacent to the supporting straps 44 and/or the bridge connection 46, this will be effective for assuring convenience in use.

Figure 13:
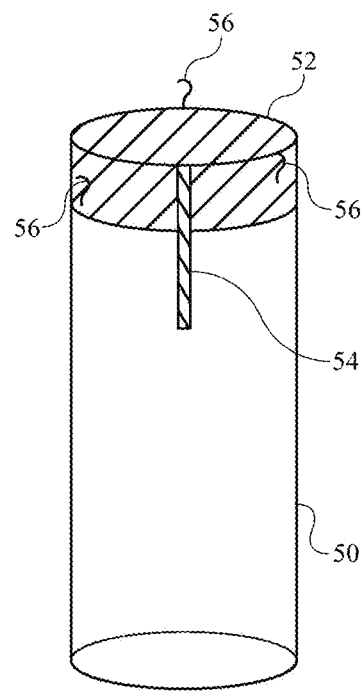
FIG. 13 is an upper perspective view illustration of an example of a supporting sleeve according to the present disclosure that is configured to receive the urine collection receptacle of FIG. 4.
Figure 14:
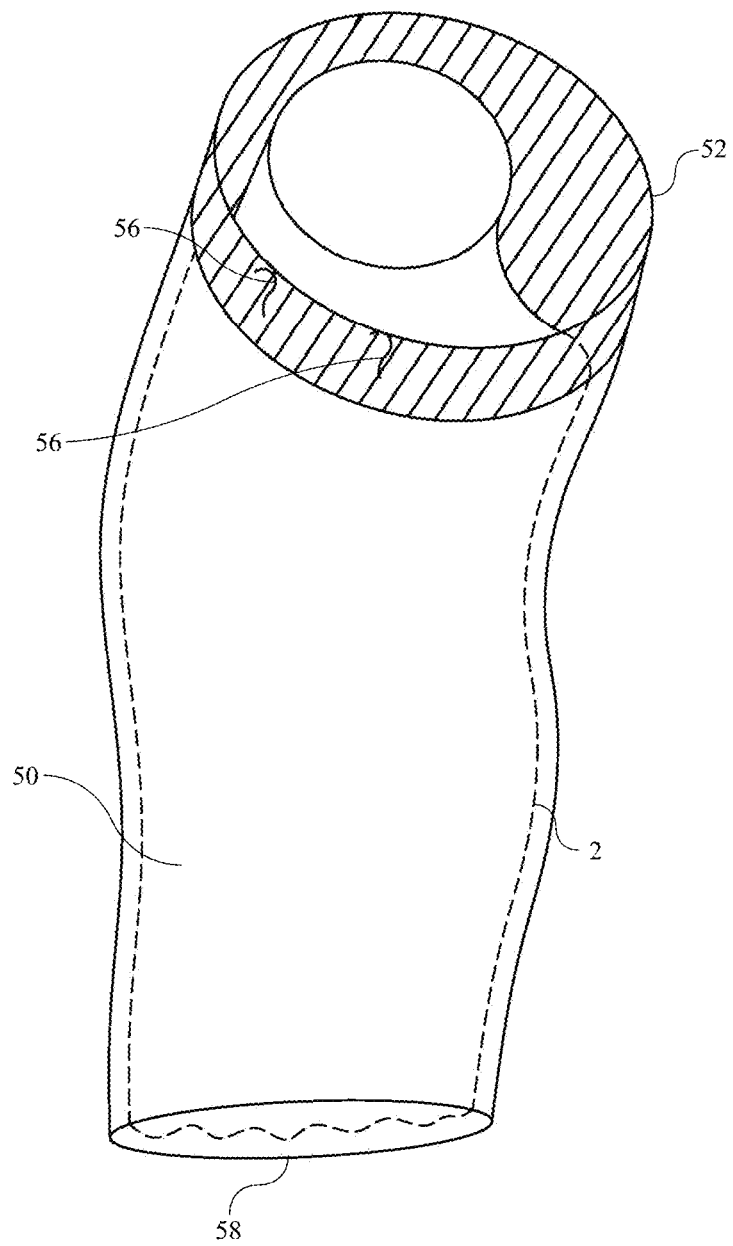
FIG. 14 is an upper perspective view illustration of the supporting sleeve of FIG. 13 showing the entrance opening of the urine collection receptacle of FIG. 4 being supported in a non-coaxial manner within an entrance opening of the supporting sleeve to define a space for a user to insert his scrotum into the supporting sleeve.

The inventor has also determined that the known wearable urinary collection apparatus 101 may also include a supporting sleeve 50 formed of fabric or the like to contain the urine collection receptacle 2 for additional support and comfort to the user. Referring to FIGS. 13-14, the supporting sleeve 50 may have an elongate tubular shape similar to the urine collection receptacle 2 so that the urine collection receptacle 2 fits securely therein without restricting the ability for the urine collection receptacle 2 to easily expand when it collects urine therein. The supporting sleeve 50 may have one open end to which the open end of the urine collection receptacle 2 may be secured, and a zipper 54 or other fastener may be provided with a portion of the supporting sleeve 50 adjacent to the open end to permit the end to be selectively expanded to facilitate insertion and removal of the urine collection receptacle 2 into and from the supporting sleeve 50. Additionally, the open end of the supporting sleeve 50 may include hooks, snaps, straps or any appropriate fastener 56 which may be used to secure the open end of the urine collection receptacle 2 (e.g., the expandable entrance opening 6) to the open end of the supporting sleeve 50 and to secure the open end of the supporting sleeve 50 to the harness 40. The size of the open end of the supporting sleeve 50 may be sufficiently large that a male user may insert his scrotum, as well as his penis or penis glans into the open end of the supporting sleeve 50. This feature helps to maintain the open end of the urine collection receptacle 2—as disposed in the supporting sleeve 50—conveniently close to the user's penis or penis glans. The open end of the urine collection receptacle 2 may be configured to comfortably receive only the user's penis or penis glans therein. The opposite end of the supporting sleeve 50 may be closed or may include some a closure that may be selectively opened or closed to expose the opposite end of the urine collection receptacle 2 or a portion thereof.

As described, the inventor has also determined that the wearable urinary collection apparatus 1 may also include a supporting sleeve (e.g., the supporting sleeve 50) formed of fabric or the like to contain the collection receptacle for additional support and comfort to the user. An exemplary implementation of the supporting sleeve 50 is shown in FIGS. 13-14. As shown, the supporting sleeve 50 may have an elongate tubular shape similar to the urine collection receptacle 2 so that the urine collection receptacle 2 fits securely therein but without restricting the ability of the urine collection receptacle 2 to easily expand when it collects urine therein. The supporting sleeve 50 may have a first open end 52 to which the open end of the urine collection receptacle 2 may be secured, and a zipper (e.g., the zipper 54) or other fastener may be provided with a portion of the supporting sleeve 50 adjacent to the first open end 52 to permit the first open end 52 to be selectively expanded to facilitate insertion and removal of the urine collection receptacle 2 into and from the supporting sleeve 50. Also, the first open end 52 of the supporting sleeve 50 may include hooks, snaps, straps, hook-and-loop fasteners or the like (e.g., the fastener 56) which may be used to secure the open end of the urine collection receptacle 2 to the first open end 52 of the supporting sleeve 50 and to secure the first open end 52 of the supporting sleeve 50 to the harness 40. The size of the first open end 52 of the supporting sleeve 50 may be sufficiently large that a male user may insert his scrotum, as well as his penis or penis glans, into the first open end 52 of the supporting sleeve 50. This may help to maintain the first open end 52 of the urine collection receptacle 2, as disposed in the supporting sleeve 50, conveniently close to the user's penis or penis glans therein. As shown in FIG. 14, for example, the expandable open end 6 of the urine collection receptacle 2 may be secured non-coaxially within the first open end 52 of the supporting sleeve 50 such that part of the first open end 52 does not have any part of the expandable open end 6 disposed therein and remains open so that the user may readily insert his scrotum into the supporting sleeve 50 through such part of the first open end 52. The inventor has determined that inserting and maintaining one's scrotum into the first open end 52 of the supporting sleeve 50 in this manner does not create any discomfort for the user. An opposite end 58 of the supporting sleeve 50 may be open as depicted to permit easy access to the lower end of the urine collection receptacle 2. Alternatively, the opposite end 58 of the supporting sleeve 50 may be closed or may include some type of closure that may be selectively opened or closed to expose the opposite end 58 of the urine collection receptacle 2 or a portion thereof.

According to a third discovery by the present inventor, the known elastomeric cap 110 as shown in FIGS. 3A-3B may not be sufficiently comfortable for a user to have provided around his penis or penis glans for an extended period of time. After doing further research, the inventor has developed a more appropriate leakage preventing cap for being provided around his penis or penis glans. Referring to FIG. 4, the leakage preventing cap 60 may be formed of a highly elastic, and tensile silicone gel material which is formed into a short tubular shape with opposite open ends. The leakage preventing cap 60 may be 2-5 cm long, have an inner diameter of 1.5-3.0 cm, and have a wall thickness of 1-3 mm. With such construction, the leakage preventing cap 60 may be easily and comfortably fitted over most user's penis or penis glans such that the leakage preventing cap 60 snugly engages the penis or penis glans, as well as the expandable entrance opening 6 of the urine collection receptacle 2 to prevent urine from leaking out of the expandable entrance opening 6, but will not create any discomfort for the user even if the leakage preventing cap 60 remains on the user's penis or penis glans for an extended period time (e.g., an hour or more).

As described the inventor has also determined that the wearable urinary collection apparatus 1 may also include more reliable and comfortable leakage preventing cap (e.g., the leakage preventing cap 60) for being provided around a user's penis or penis glans prior to the penis or penis glans being inserted into the expandable entrance opening 6, such as shown in FIG. 5. The leakage preventing cap 60 is a separate member which is simply fitted around the user's penis or penis glans but not connected to the urine collection receptacle 2 or any other part of the wearable urinary collection apparatus 1. The leakage preventing cap 60 may be formed of a highly elastic, and tensile silicone gel material which is formed into a short tubular shape with opposite open ends. The leakage preventing cap 60 may be 2-5 cm long, have an inner diameter of 1.5 to 3 cm, and have a wall thickness of 1-3 mm. With such construction the leakage preventing cap 60 may be easily and comfortably fitted over most user's penis or penis glans such that the leakage preventing cap 60 snugly engages the penis or penis glans, as well as the expandable entrance opening 6 of the urine collection receptacle 2, to prevent urine from leaking out of the entrance opening 6, but will not create any discomfort for the user even if the leakage preventing cap 60 remains on the user's penis or penis glans for an extended period (e.g., an hour or more).

As described previously, FIG. 10 shows an example of the expandable entrance opening 6' that is not formed directly into the one end of the urine collection receptacle 2, as is done in the implementation of FIGS. 4 and 7A-7C, but rather the expandable entrance opening 6' is initially provided in a separate member 30, which is formed of plastic sheet material such as used in forming the urine collection receptacle 2, and then the separate member 30 is attached to the urine collection receptacle 2 at its one open end using heat, energy pulses, adhesive or other appropriate means. The separate member 30 having the expandable entrance opening 6' may be formed similarly to how the expandable entrance opening 6 is formed with reference to FIGS. 7A-7C using the small elastic band 22, the planar, somewhat rigid member 20, and a short tubular member formed of plastic sheet material having an ID corresponding to that of the urine collection receptacle 2, e.g., the planar, somewhat rigid member 20 may be inserted into the tubular member, the small elastic band 22 may be placed around the tubular member where the planar, somewhat rigid member 20 is located, the tubular member may be folded itself from one end toward the other, and then the planar, somewhat rigid member 20 may be removed, thereby defining the expandable entrance opening 6' at one end of the folded tubular member. When the separate member 30 is connected to the open end of the urine collection receptacle 2, a lower open end of the separate member 30 opposite to the expandable entrance opening 6', may be connected to the open upper end of the urine collection receptacle 2 slightly inward of the edge of open end where the broken line extends in FIG. 10 using heat, energy pulses or the like and such that the lower end of the folded tubular member is spaced away from the closest one of the backflow preventing means 4.

Figure 11:
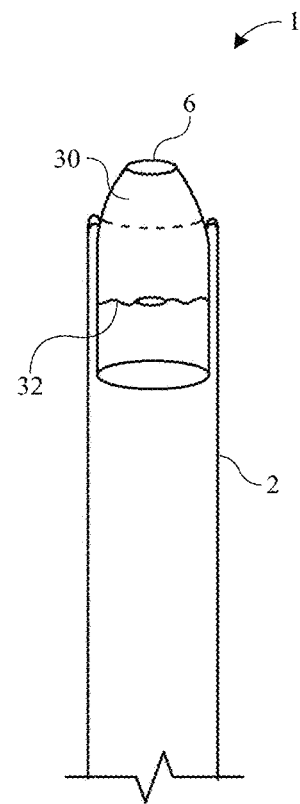

The connection between the separate member 30 and the urine collection receptacle 2 may not create any constriction to the ID of the collection receptacle such as in FIG. 10, but it is possible to create a constriction at such connection. For example, FIG. 11 shows a modification to structure of FIG. 10 wherein the separate member 30 is connected to the urine collection receptacle 2 at an axially intermediate part of the separate member via a constriction 32 which reduces the ID of the collection receptacle to about ⅓ to ⅕ of its original size, and such that a portion of the separate member 30 apposite to the expandable opening 6' extends inward of the constriction 32. With this modification, the constriction 32 and the lower portion of the separate member 30 may act as a type of backflow preventing means with or without one or more of the backflow preventing means 4 disposed inward of the separate member 30 within the urine collection receptacle 2.

Figure 15:
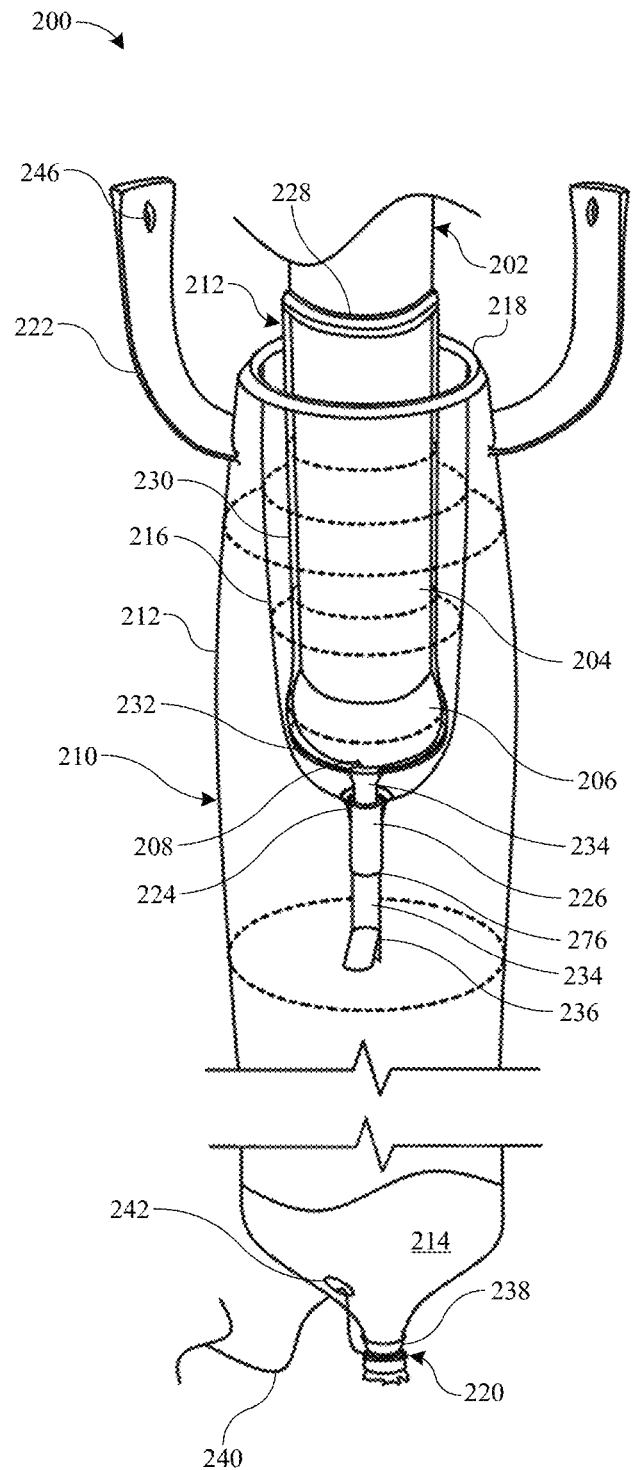
FIG. 15 is an upper perspective view illustration of an example of a wearable urinary collection apparatus according to the present disclosure including an inner collection member disposed within a redundant urine collection area of a urine collection receptacle, in which certain components are shown as hidden or transparent, indicated by broken lines, for clarity.

FIG. 15 is an upper perspective view illustration of an example of a wearable urinary collection apparatus 200 according to the present disclosure. The wearable urinary collection apparatus 200 comprises a urine collection receptacle 210 and an inner collection member 212 that are cooperatively configured to efficiently collect and store urine while ensuring user comfort and hygiene. As described in greater detail below, the inner collection member 212 may be disposed within a redundant urine collection area of the urine collection receptacle 210 such that a stream guide tube extending from an end of the inner collection member 212 extends into the urine collection receptacle 210 to form a fluid-flow path from the inner collection member 212 directly into the urine collection receptacle 210. Through careful study of existing technologies, such as the known wearable urinary collection apparatus 101 and the wearable urinary collection apparatus 1, the inventor has developed certain improvements to address critical aspects such as user comfort, backflow prevention, leak prevention, manufacturability, and reusability.

The wearable urinary collection apparatus 200 represents a significant advancement over previous implementations, incorporating innovative features to enhance its overall performance and user experience. The urine collection receptacle 210 and the inner collection member 212 are configured with a focus on efficient urine storage and leak prevention, and may be constructed from flexible, durable materials that may comfortably conform to the user's body while maintaining structural integrity.

As described in further detail below, an improvement of the wearable urinary collection apparatus 200 is the incorporation of one or more mechanisms, such as one-way valves or strategically placed constrictions, to ensure that urine flows only in the intended direction—from the user into the urine collection receptacle 210. Furthermore, manufacturability has been carefully considered in the wearable urinary collection apparatus 200. The components thereof, as described in further detail below, may be configured for ease of assembly and cost-effective production. Finally, reusability is another important aspect addressed in this improved implementation. While some components may be disposable for hygiene reasons, the overall structure of the wearable urinary collection apparatus 200 may be configured to be durable and easy to clean. This approach not only reduces waste but also makes the device more economical for long-term use.

The wearable urinary collection apparatus 200 may be configured for both ambulatory and stationary applications. This flexibility ensures that the device is suitable for a wide range of users, including those with temporary or permanent mobility issues, as well as individuals in various occupational settings where access to traditional restroom facilities may be limited.

FIG. 15 is an upper perspective view illustration of the wearable urinary collection apparatus 200. The inner collection member 212 may be configured to receive at least a portion of a length of a penis 202 of a user. The inner collection member 212 may extend longitudinally from an upper end to a lower end. The inner collection member 212 may include a penile sleeve 230 configured to extend along a shaft 204 of the penis 202. The penile sleeve 230 may extend from a voiding area 232 (e.g., an end portion of the inner collection member 212) toward the upper end of the inner collection member 212. The voiding area 232 may be disposed at the lower end of the inner collection member 212 and may be configured to be in close proximity (e.g., adjacent) to a penis glans 206 and/or a urethral opening 208 of the penis 202. In other words, the voiding area 232 (e.g., an end portion of the inner collection member 212) may be configured to extend around the penis glans 206 of the penis 202. This strategic placement of the voiding area 232 allows for efficient capture of the urinary fluid 214 as it is voided, directing it immediately into the urine collection receptacle 210 and minimizing the risk of leakage or backflow.

The inner collection member 212 may include a stream guide tube 234 extending from the voiding area 232 away from the upper end. In some implementations, the voiding area 232 may be configured to be adjacent to a penis glans 206 of the penis 202. In some implementations, the stream guide tube 234 may be configured to be adjacent to a terminal end of the penis 202, such as the urethral opening 208. The stream guide tube 234 may be formed from or comprise a flexible elastomer and/or may be relatively rigid. In some implementations, the stream guide tube 234 may be about 5 cm long and may have an inside diameter of about 1.0 cm. The stream guide tube 234 is configured to efficiently direct the urinary fluid 214 from the voiding area 232 into the urine collection receptacle 210 by ensuring that urine is guided directly into the urine collection receptacle 210 without risk of leakage or backflow. One or both of the voiding area 232 and the stream guide tube 234 may be formed from or comprise a silicon membrane, an elastomer, or a combination thereof.

In some implementations, the stream guide tube 234 may include a one-way valve 236 disposed at a terminal end thereof. The one-way valve 236 may be or comprise a thin (e.g., 1-2 mil) polymer tube that is about 2-4 cm long and flexible. The one-way valve 236 may be formed from or comprise the same material as that of the urine collection receptacle 210. As shown, in some implementations, the one-way valve 236 may comprise a flexible sheet adjacent to an opposing surface. The flexible sheet may be biased toward the opposing surface when the urinary fluid 214 is not flowing through the stream guide tube 234 to inhibit the urinary fluid 214 from traveling through the stream guide tube 234 from within the urine collection receptacle 210. When the urinary fluid 214 flows through the stream guide tube 234, the flexible sheet may be urged away from the opposing surface to enable the urinary fluid 214 to travel through the stream guide tube 234 from the inner collection member 212. In other words, when the user voids themself of the urinary fluid 214, the pressure of the flowing fluid pushes the flexible sheet away from the opposing surface, allowing the urine to pass therethrough into the urine collection receptacle 210. As explained in further detail below, the one-way valve 236 may be inserted through a contractile stem tube of the urine collection receptacle 210 during assembly, which may form a constriction along the stream guide tube 234. Alternatively, as also explained in further detail below, the one-way valve 236 may be connected to the terminal end of a tubular port of a redundant urine collection area of the urine collection receptacle 210.

The material composition and structural characteristics of the stream guide tube 234 and the voiding area 232 are carefully considered to balance flexibility and rigidity. For example, the relative rigidity of the stream guide tube 234 may be important for maintaining its shape and ensuring a consistent urine flow direction, even under varying pressures or user movements. The 5 cm length of the stream guide tube 234 may provide sufficient distance to guide the urinary fluid 214 from the penis 202 into the urine collection receptacle 210, while the 1.0 cm inside diameter of the stream guide tube 234 may allow for adequate flow capacity without being overly large or cumbersome. An upper band 228 may be included near the upper end of the inner collection member 212 (e.g., opposite the voiding area 232). In some implementations, the upper band 228 may help secure the inner collection member 212 to the penis 202 (e.g., may aid in rolling the inner collection member 212 onto the penis 202).

Figure 16A:
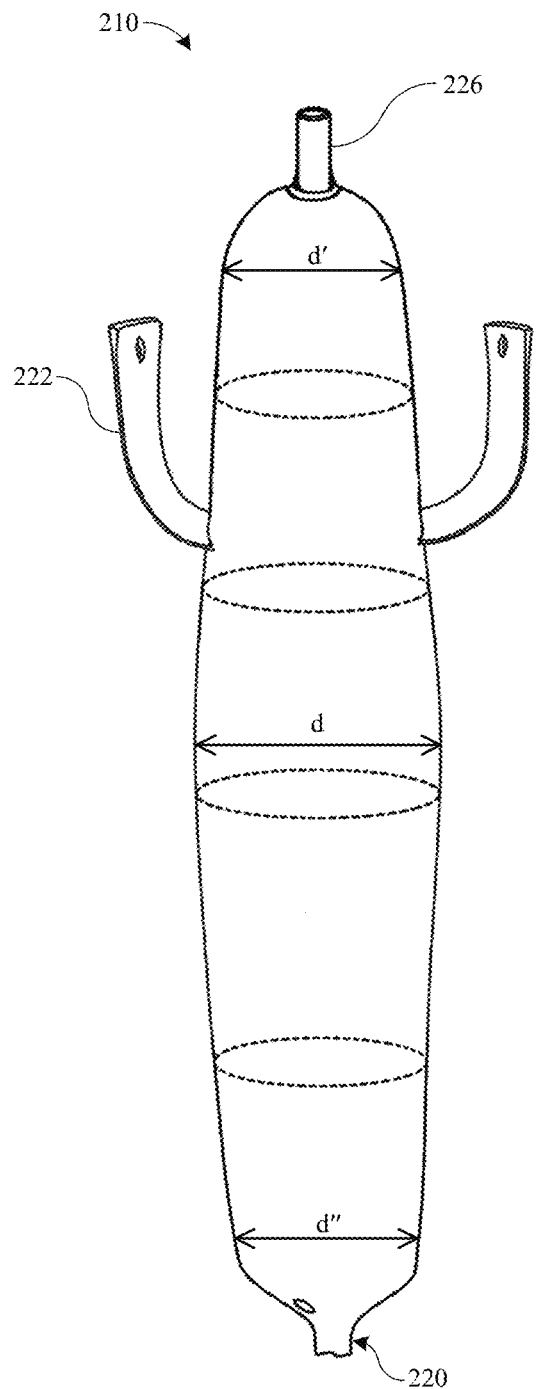
FIGS. 16A-16C are upper perspective view illustrations of the wearable urinary collection apparatus of FIG. 15 demonstrating an example of a method for forming the redundant urine collection area and inserting the inner collection member into the redundant urine collection area, in which certain components are shown as hidden or transparent, indicated by broken lines, for clarity.

FIG. 16A is an upper perspective view illustration of the urine collection receptacle 210 prior to formation of a redundant urine collection area (described below). The urine collection receptacle 210 may be configured to collect urinary fluid 214 therein. As best shown in FIG. 16A, in some implementations, the urine collection receptacle 210 may comprise or be formed from a tube of flexible polymer film (e.g., membrane) with a thickness of about 3 mil (e.g., about 0.075 cm). The urine collection receptacle 210 may have a flat lying width of about 11 cm and a length (measured orthogonal to the width) of about 80 cm. Accordingly, in some implementations, the urine collection receptacle 210 may be referred to as a membrane (e.g., a tubular membrane, etc.). The urine collection receptacle 210 may extend longitudinally from an upper end to a lower end. As shown in FIG. 16A, the urine collection receptacle 210 may have an elongated tubular structure with varying diameters (e.g., d, d', d", etc.) along its length.

The urine collection receptacle 210, the inner collection member 212, and/or components thereof may comprise or be formed from a thin membrane that is generally impermeable to resistant to the urinary fluid 214. For example, in some implementations, the urine collection receptacle 210, the inner collection member 212, and/or components thereof may comprise or be formed from a thermoplastic polyurethane (TPU) membrane. The use of thermoplastic polyurethane may provide benefits such as durability, flexibility, and ease of cleaning, which may contribute to the overall reusability of the wearable urinary collection apparatus 200. For example, the durability of TPU may ensure that the urine collection receptacle 210 and/or the inner collection member 212 are capable of withstanding repeated use and the stresses associated therewith, which may reduce the need for frequent replacements. The flexibility of TPU may also allow the urine collection receptacle 210 and/or the inner collection member 212 to conform to the user's body movements, enhancing comfort and reducing the risk of leaks. Additionally, TPU's smooth surface and chemical resistance make it easy to clean and disinfect, which is crucial for maintaining hygiene in a reusable urinary collection apparatus, such as the wearable urinary collection apparatus 200.

Figure 16B:
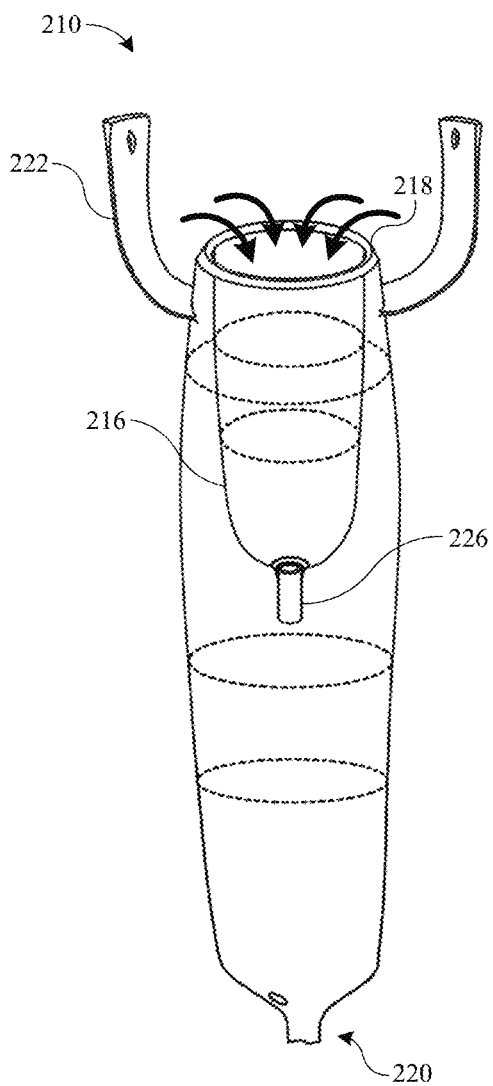
Figure 16C:
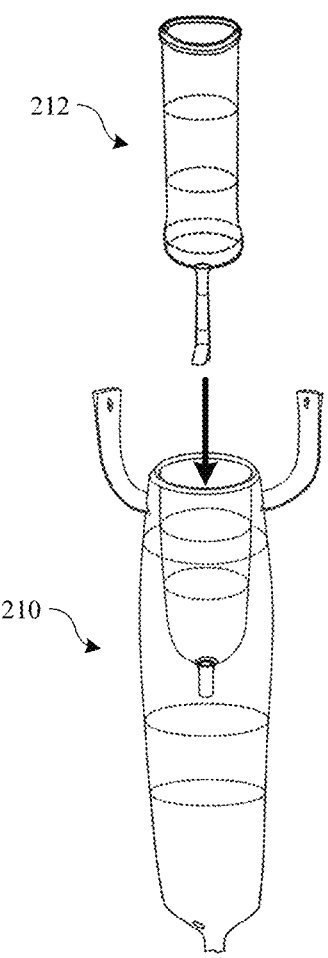

Referring to FIGS. 15-16C, the urine collection receptacle 210 may include the redundant urine collection area 216 (e.g., a redundant fluid collection portion) at the upper end configured to receive the inner collection member 212. In other words, the urine collection receptacle 210 may include the redundant urine collection area 216 that is configured to extend around the inner collection member 212 or a portion (e.g., a length) thereof.

FIG. 16B is an upper perspective view illustration of the urine collection receptacle 210 demonstrating a method for forming the redundant urine collection area 216 according to an example. As shown, the redundant urine collection area 216 may be formed by inverting the upper end of the urine collection receptacle 210 inwards at an inversion 218 (depicted in FIG. 16B by bolded arrows) such that once inverted, the urine collection receptacle 210 extends upwards from the lower end and terminates at the inversion 218. Furthermore, as explained below with reference to FIGS. 18-20, in some implementations, the redundant urine collection area 216 may be formed by inverting the upper end of the urine collection receptacle 210 inwards over a rounded rim (e.g., an inner collection ring described below). In the illustrated implementation it may appear as though the inversion 218 is a rigid structure; however, as explained previously, due to the urine collection receptacle 210 being formed from a thin membrane (e.g., a TPU membrane), the inversion 218 may be substantially compliant and flexible, such that, for example, the upper end of the redundant urine collection area 216 may be collapsable under clothes (e.g., a shirt) of the user.

The redundant urine collection area 216 may extend into the urine collection receptacle 210 to a depth of about 20 cm or longer (e.g., such that a distance between the inversion 218 and an apex of the redundant urine collection area 216 is about 20 cm or longer). The redundant urine collection area 216 serves multiple functions. For example, by inverting the upper end of the urine collection receptacle 210 inwards at the inversion 218, a double-walled section is formed at the top of the urine collection receptacle 210. This inverted section forms a pocket-like area that may accommodate the inner collection member 212, allowing for a secure connection between the two main components of the wearable urinary collection apparatus 200 at an interface 276.

The depth of approximately 20 cm or longer for the redundant urine collection area 216 (e.g., the apex of the redundant urine collection area 216) may be significant for several reasons. Firstly, this depth provides ample space to envelop the inner collection member 212 (e.g., to envelope all of the inner collection member 212 or a portion, such as a length, thereof). This depth also creates additional volume within the urine collection receptacle 210, effectively increasing its overall capacity for collection of the urinary fluid 214. Moreover, the redundant urine collection area 216 may act as a safeguard against potential leaks. For example, if any of the urinary fluid 214 were to escape past the primary seal formed by the interface 276 between the urine collection receptacle 210 and the inner collection member 212 (e.g., a stream guide tube 234 and a contractile stem tube 226 described below), it would be contained within this secondary collection area. Finally, due to the flexible nature of the redundant urine collection area 216 (e.g., formed from thin polymer material), the redundant urine collection area 216 may be configured to allow movement of the urine collection receptacle 210 relative to the user by deforming to enable the inner collection member 212 to move relative to the urine collection receptacle 210 without compromising the seal formed between the inner collection member 212 and the urine collection receptacle 210 at the interface 276.

The urine collection receptacle 210 may include a tubular port 224 disposed within the redundant urine collection area 216 (e.g., at an apex of the redundant urine collection area 216) configured to receive the stream guide tube 234 of the inner collection member 212. In some implementations, the tubular port 224 may be formed from or comprise thin contractile rubber. In some implementations, a contractile stem tube 226 may be disposed within the tubular port 224. Where the urine collection receptacle 210 include the contractile stem tube 226, one or both of the contractile stem tube 226 and the tubular port 224 may be formed from or comprise thin contractile rubber. The contractile stem tube 226 and/or the tubular port 224 may extend into the urine collection receptacle 210 when the upper end thereof is inverted to form the redundant urine collection area 216. The combination of the stream guide tube 234 and the contractile stem tube 226 and/or the tubular port 224 may provide a secure connection between the inner collection member 212 and the urine collection receptacle 210 at an interface 276. The interface 276 may be configured to prevent leaks (e.g., from within the urine collection receptacle 210 into the redundant urine collection area 216).

FIG. 16C is an upper perspective view illustration of the urine collection receptacle 210 demonstrating a method for inserting the inner collection member 212 into the redundant urine collection area 216 according to an example. As shown, the inner collection member 212—initially positioned above the urine collection receptacle 210—may be moved (e.g., translated) downward toward the urine collection receptacle 210 and into the redundant urine collection area 216. When the inner collection member 212 is received in the redundant urine collection area 216, the stream guide tube 234 may extend through the contractile stem tube 226 and/or the tubular port 224 into the urine collection receptacle 210 to define a fluid flow path from the voiding area 232 to the urine collection receptacle 210. As described previously, the one-way valve 236 may be disposed at an end (e.g., a terminal end) of the stream guide tube 234 opposite the voiding area 232 and may be configured to inhibit the urinary fluid 214 from backflowing from the urine collection receptacle 210 through the stream guide tube 234.

The stream guide tube 234 may also be configured to ensure that the urinary fluid 214 is guided directly into the urine collection receptacle 210 without risk of leakage or backflow. When the inner collection member 212 is properly inserted into the redundant urine collection area 216, the stream guide tube 234 may pass through the contractile stem tube 226 such that the terminal end thereof (e.g., the one-way valve 236) is disposed within the urine collection receptacle 210, creating a secure pathway for the urinary fluid 214 to flow from the user directly into the urine collection receptacle 210. The interface 276 between the contractile stem tube 226 and the stream guide tube 234 may be configured to create a seal that inhibits the movement of collected urine from the main body of the urine collection receptacle 210 into the redundant urine collection area 216. This cooperative sealing action is crucial for maintaining the efficiency of the system and preventing unnecessary filling of the redundant area.

The tubular port 224 of the urine collection receptacle 210 may be formed from or comprise the same material as a remainder of the urine collection receptacle 210 (e.g., may be formed from or comprise a TPU membrane). In some implementations, however, the tubular port 224 may be formed from or comprise a different material than that of the remainder of the urine collection receptacle 210. For example, the tubular port 224 may be formed from or comprise a tubular elastomer that is connected to or formed integrally with the urine collection receptacle 210 (e.g., at an apex of the redundant urine collection area 216). In some implementations, an inner diameter of the tubular port 224 (e.g., a relaxed inner diameter of the tubular port 224) may be smaller than an outer diameter of the contractile stem tube 226 (e.g., a relaxed outer diameter of the tubular port 224) such that the contractile stem tube 226 is securable within the tubular port 224.

Furthermore, the contractile nature of the tubular port 224 may enable the tubular port 224 to grip the contractile stem tube 226, forming a seal therebetween that inhibits leaks at the interface between these components (e.g., from within the urine collection receptacle 210 into the redundant urine collection area 216). The combination of the tubular port 224 and the contractile stem tube 226 may form a multi-layered barrier against leaks and backflow. The contractile properties of the tubular port 224 and/or the contractile stem tube 226 may also allow passive adjustment to movement or changes in pressure, maintaining their sealing effectiveness during user activity.

The contractile stem tube 226 may comprise a tubular elastomer that has a relaxed inner diameter that is smaller than an outer diameter of the stream guide tube 234. Accordingly, in some implementations, the contractile stem tube 226 may also be operable to form a constriction along the stream guide tube 234 when the stream guide tube 234 is inserted therethrough. In implementations where the tubular port 224 comprises a tubular elastomer, the stream guide tube 234 and the tubular port 224 may cooperatively form the constriction along the stream guide tube 234. The constriction formed along the stream guide tube 234 may be configured to enable only unidirectional flow of the urinary fluid 214 from the inner collection member 212 to the urine collection receptacle 210. Stated differently, the constriction formed along the stream guide tube 234 may enable the urinary fluid 214 to flow from the inner collection member 212 to the urine collection receptacle 210, and may inhibit (e.g., prevent) the urinary fluid 214 from flowing from the urine collection receptacle 210 to the inner collection member 212. For example, as the inner collection member 212 is inserted into the redundant urine collection area 216, the stream guide tube 234 may pass through the contractile stem tube 226 and/or the tubular port 224. As the urinary fluid 214 flows through the stream guide tube 234, the contractile stem tube 226 constricts therearound, creating a dynamic seal that adapts to changes in pressure and flow. This constriction helps prevent urine from flowing back up the stream guide tube 234 towards the user, even if the urine collection receptacle 210 is subjected to external pressure or movement.

In some implementations, select surfaces of the wearable urinary collection apparatus 200 may be coated with hydrogel to provide additional protection against backflow and leakage. For example, the inner surface of the inversion 218, the upper portion of the redundant urine collection area 216, and/or the upper band 228 of the inner collection member 212 may be coated with hydrogel to further inhibit leakage of the urinary fluid 214 from the inner collection member 212 and/or the urine collection receptacle 210. Furthermore, in some implementations, an adaptor (not shown) comprising a female pad with a duct may be connected to the tubular port 224 for use by females. This adaptor may allow the wearable urinary collection apparatus 200 to be used by individuals without a penis. By incorporating both active (constriction) and passive (redundant collection area) measures, the configuration aims to provide reliable performance under various conditions and user movements. This comprehensive approach to fluid management is essential for ensuring user comfort, maintaining hygiene, and preventing potential embarrassment or discomfort that could arise from leaks or backflow.

Still referring to FIGS. 15-16C, the urine collection receptacle 210 may include elongate mating members 222 that extend generally away therefrom (e.g., generally away from an upper portion of the urine collection receptacle 210). In some implementations, the elongate mating members 222 may be connected to an outer surface of the urine collection receptacle 210 using an adhesive or the like. The elongate mating members 222 may include mating features 246 that are removably couplable to complementary mating features of a harness (described below). This configuration may allow for easy attachment and detachment of the urine collection receptacle 210 to and from the harness, facilitating cleaning and replacement when necessary. Although the mating features 246 are illustrated as apertures that extend through the elongate mating members 222, any suitable type of coupling or geometry may be used (e.g., snaps, magnets, hooks, etc.).

The urine collection receptacle 210 may include also include a discharge port 220 at a lower end thereof (e.g., opposite the upper end). The discharge port 220 and associated mechanisms described below may allow for controlled emptying of the urinary fluid 214 from the urine collection receptacle 210, enhancing the overall usability of the wearable urinary collection apparatus 200.

In some implementations, the discharge port 220 may include an open-close mechanism 238. The open-close mechanism 238 may comprise a small rubber ring band wrapped around a key ring. A cord 240 may be attached to the key ring for balancing the pulling weight of the urinary fluid 214 accumulated within the urine collection receptacle 210. For example, as the urinary fluid 214 collects in the urine collection receptacle 210, the weight distribution of the wearable urinary collection apparatus 200 may change, potentially causing discomfort or altering the fit of the wearable urinary collection apparatus 200 or portions thereof. Accordingly, the cord 240 may enable the user to adjust the position of the urine collection receptacle 210, ensuring comfort and proper alignment throughout use. Furthermore, the cord 240 may enhance the accessibility of the discharge port 220 by, for example, enabling users to locate and manipulate the open-close mechanism 238 more easily. This feature is particularly beneficial for users with mobility limitations or those who require assistance in managing the device. In some implementations, the urine collection receptacle 210 may include a cord aperture 242 through which the cord 240 may extend to further support the cord 240 with respect to the urine collection receptacle 210.

As best shown in FIG. 16A, the lower portion of the urine collection receptacle 210 may taper to the discharge port 220. The tapering of the lower portion of the urine collection receptacle 210 towards the discharge port 220 may facilitate the controlled emptying of the urine collection receptacle 210. This tapering may help direct the flow of urine towards the discharge port when the user is ready to empty the receptacle. Where the urine collection receptacle 210 has a shorter length, the tapering of the lower portion of the urine collection receptacle 210 may not be necessary to direct the flow of the urinary fluid 214 to the discharge port 220, and accordingly may not be included.

Figure 17:
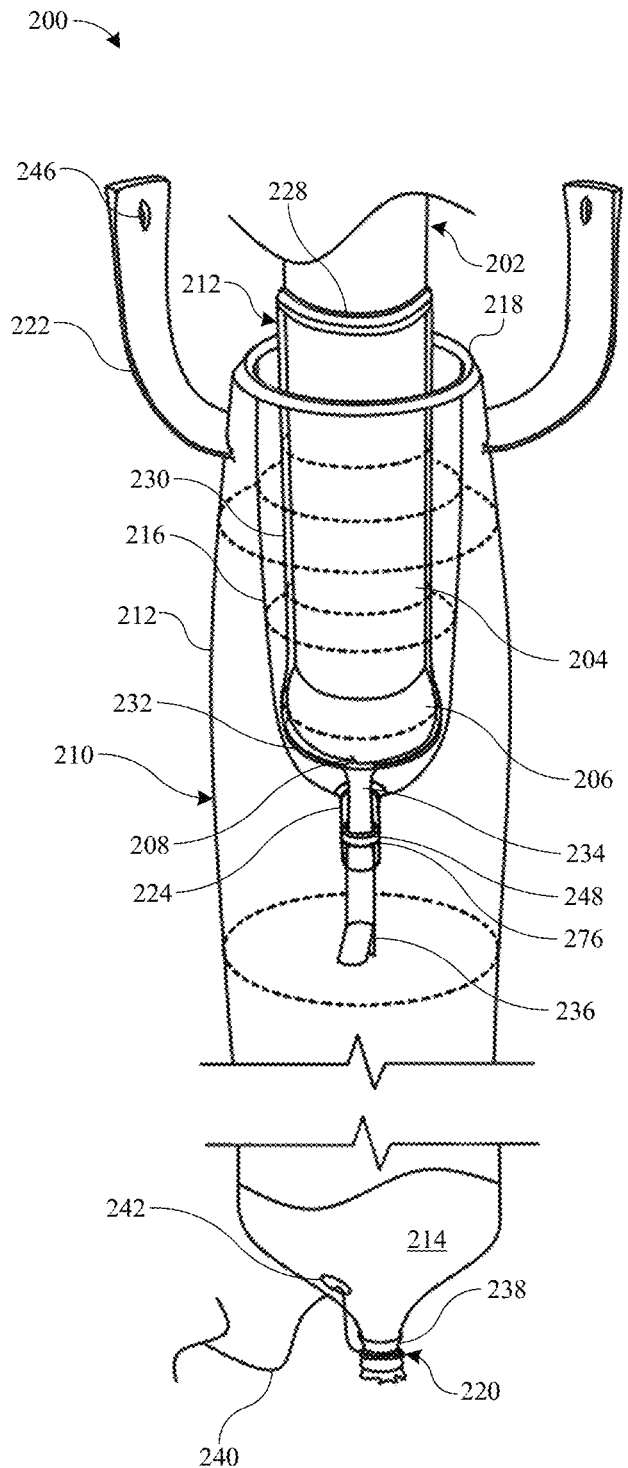
FIG. 17 is an upper perspective view illustration of another example of the wearable urinary collection apparatus of FIG. 15 in which the urine collection receptacle includes a contractile ring, and in which certain components are shown as hidden or transparent, indicated by broken lines, for clarity.

FIG. 17 is an upper perspective view illustration of another example of the wearable urinary collection apparatus 200 according to the present disclosure. The wearable urinary collection apparatus 200 may include variations and additional features as compared to the implementation shown in FIG. 15. For example, in the illustrated implementation, the wearable urinary collection apparatus 200 includes a contractile ring 248 rather than the contractile stem tube 226. The contractile ring 248 may be disposed within the tubular port 224 of the urine collection receptacle 210 (e.g., disposed centrally along a length of the tubular port 224. The contractile ring 248 may provide an alternative means of creating a seal between the inner collection member 212 (e.g., the stream guide tube 234) and the urine collection receptacle 210 at the interface 276. This configuration may offer benefits such as easier assembly or improved sealing in certain situations. The contractile ring 248 may be made of a flexible, elastic material that may conform to the shape of the stream guide tube 234, creating a tight seal to prevent leaks and backflow. Similar to the contractile stem tube 226, the contractile ring 248 may have an relaxed inner diameter that is smaller than a relaxed outer diameter of the stream guide tube 234 such that the contractile ring 248 is configured to form a constriction along the stream guide tube 234 that functions similarly the constriction formed from the contractile stem tube 226 described previously.

The use of the contractile ring 248, as opposed to the tubular structure of the contractile stem tube 226, may offer several advantages. Firstly, the contractile ring 248 may streamline the assembly process of the wearable urinary collection apparatus 200 by allowing for easier insertion of the stream guide tube 234, potentially reducing the time and complexity involved in assembling the wearable urinary collection apparatus 200. This could be particularly beneficial in clinical settings where rapid assembly might be necessary. Additionally, the contractile ring 248 may provide improved sealing performance in certain situations, for example, by concentrating pressure at a specific point along the stream guide tube 234 to form more localized and potentially stronger seal at the interface 276. This could be especially advantageous in ambulatory scenarios where the user's movements or changes in body position might put stress on the connection between the inner collection member 212 and the urine collection receptacle 210.

Figure 18:
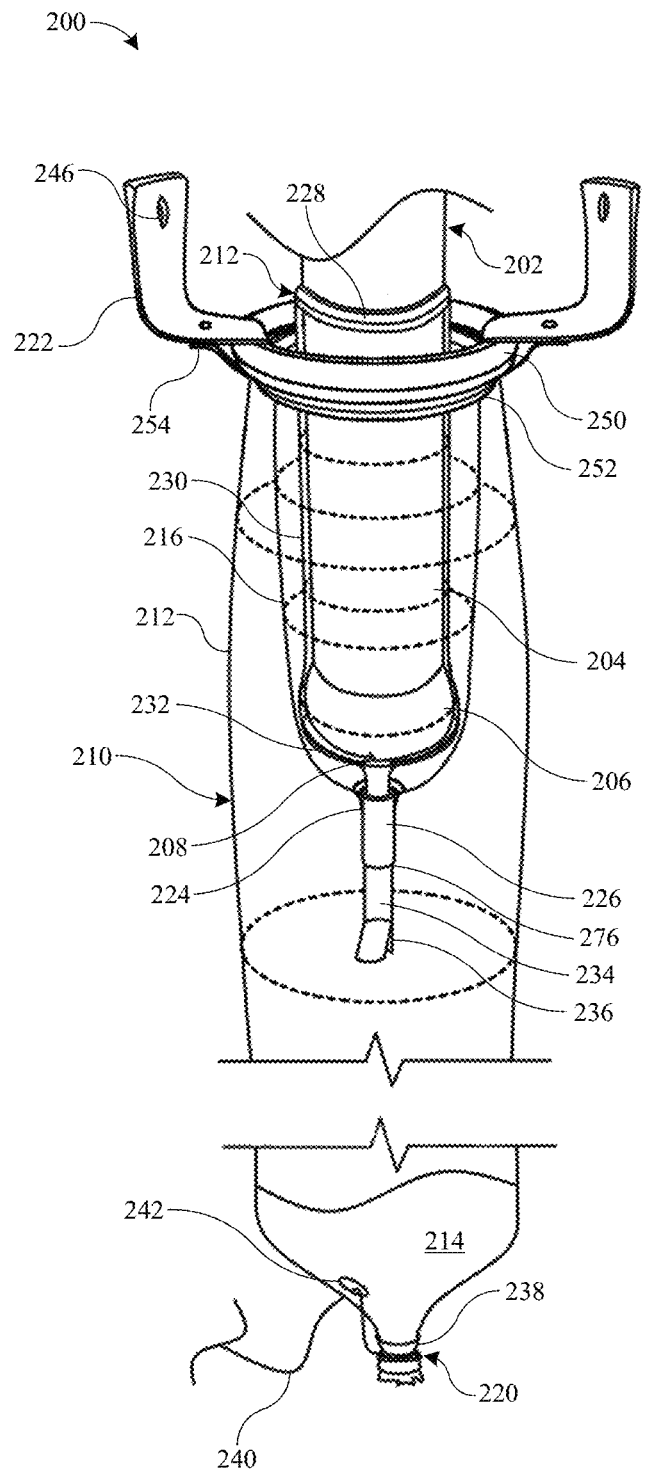
FIG. 18 is an upper perspective view illustration of another example of the wearable urinary collection apparatus of FIG. 15 in which the urine collection receptacle includes an outer adaptor ring connected to an inner opening ring, and in which certain components are shown as hidden or transparent, indicated by broken lines, for clarity.

FIG. 18 is an upper perspective view illustration of another example of the wearable urinary collection apparatus 200 according to the present disclosure. The wearable urinary collection apparatus 200 may include variations and additional features as compared to the implementation shown in FIG. 15. For example, in the illustrated implementation, the wearable urinary collection apparatus 200 includes an outer adaptor ring 250 and an inner opening ring 252. In some implementations, one or both of the outer adaptor ring 250 and the inner opening ring 252 may be formed from or comprise a semi-rigid material (e.g., an elastomeric rubber or the like). For example, one or both of the inner opening ring 252 and the outer adaptor ring 250 may be substantially compliant and flexible, such that, for example, the upper end of the redundant urine collection area 216 may be collapsable under clothes (e.g., a shirt) of the user. In some implementations, the inner opening ring 252 may include grooves and/or ridges applied circumferentially around the inversion 218 of the urine collection receptacle 210 configured for releasable connection with the outer adaptor ring 250 to form a secure attachment therebetween. The outer adaptor ring 250 may include fastening means to which the elongate mating members 222 may be connected. In such an implementation, the outer adaptor ring 250 may be configured to interface with (e.g., may include features for interfacing with) the elongate mating members 222. For example, the elongate mating members 222 may include loops 254 that are configured to extend around the outer adaptor ring 250.

In some implementations, the inner opening ring 252 may be configured to maintain the shape of the inversion 218 and/or the redundant urine collection area 216 while providing a compliant (e.g., elastic) structure that may enhance user comfort. As described previously, in some implementations, the redundant urine collection area 216 of the urine collection receptacle 210 may be formed by inverting the upper portion of the urine collection receptacle 210 (e.g., an upper end of the urine collection receptacle 210) over the inner opening ring 252 such that the inversion 218 is formed over the inner opening ring 252. In such an implementation, the inversion 218 may be rounded as it extends over the inner opening ring 252.

Where the inner opening ring 252 include the grooves and/or ridges for connection with the outer adaptor ring 250, the groove and/or ridges may be applied circumferentially around the inversion 218 of the urine collection receptacle 210. These grooves and/or ridges may serve several functions, such as providing a mechanical interlock with the outer adaptor ring 250 to ensure a secure connection that may distribute the weight of the urine collection receptacle 210 evenly around the circumference of the inversion 218. Additionally, the inner opening ring 252 may aid in maintaining the shape of the inversion 218, which may be important for the proper functioning of the redundant urine collection area 216 (e.g., to prevent collapse of the redundant urine collection area 216). In implementations where the inner opening ring 252 is disposed beneath the inversion 218 (e.g., where the redundant urine collection area 216 is formed by folding the upper end thereof over the inner opening ring 252), the ridges and/or grooves may be so distinct as to be defined (e.g., connectable) through the material that forms the urine collection receptacle 210 (e.g., a TPU membrane).

In implementations where the urine collection receptacle 210 includes the inner opening ring 252, the wearable urinary collection apparatus 200 may include a urine receptacle bag (not shown) rather than the urine collection receptacle 210. In such an implementation, the urine receptacle bag may be configured to collection the urinary fluid 214 therein and may be formed as an independent member (e.g., rather than being formed by inverting the upper portion of the urine collection receptacle 210 inwards) that extends downward from the inner opening ring 252. For example, the redundant urine collection area 216 may extend downward from the circumference of the inner opening ring 252. The urine receptacle bag may also extend from the inner opening ring 252 (e.g., the circumference of the inner opening ring 252) outward of the redundant urine collection area 216 and may extend fully around the redundant urine collection area 216 (e.g., may fully envelop the redundant urine collection area 216). In some implementations, the urine receptacle bag and/or the redundant urine collection area 216 may be removably connectable to the inner opening ring 252 to form respective seals therebetween. The urine receptacle bag may be formed from the same material(s) as described previously with respect to the urine collection receptacle 210. Accordingly, this implementation of the wearable urinary collection apparatus 200 may function substantially similarly to other implementations of the wearable urinary collection apparatus 200 described herein.

Figure 19A:
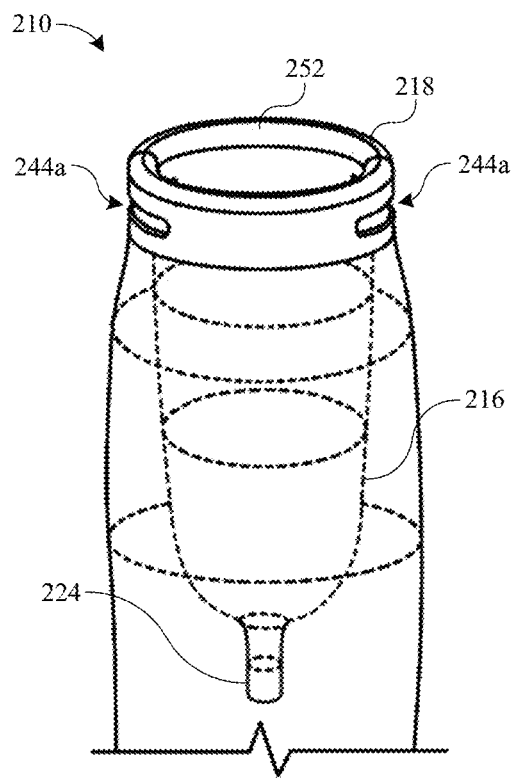
FIG. 19A is an upper perspective view illustration of another example of the urine collection receptacle of FIG. 15 including an example of mating features for connection with elongate members, in which certain components are shown as hidden or transparent, indicated by broken lines, for clarity.
Figure 19B:
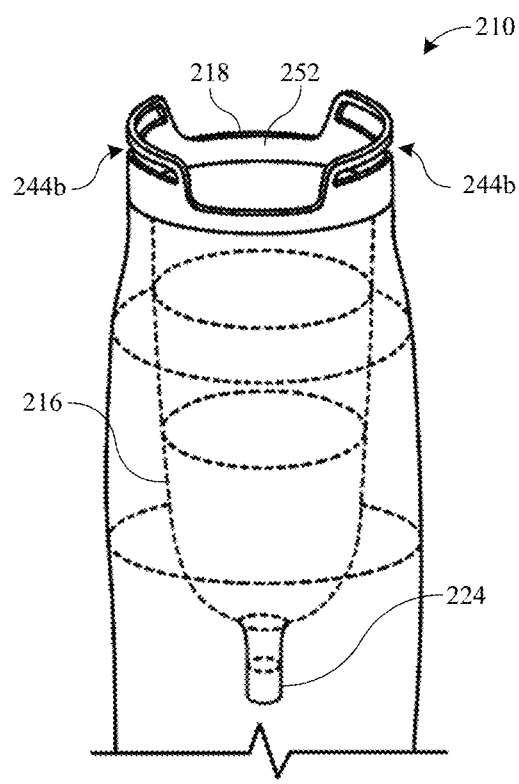
FIG. 19B is an upper perspective view illustration of another example of the urine collection receptacle of FIG. 15 including another example of the mating features for connection with the elongate mating members, in which certain components are shown as hidden or transparent, indicated by broken lines, for clarity.

FIGS. 19A-19B are upper perspective view illustrations of other examples of the urine collection receptacle 210. As shown, in some implementations, the urine collection receptacle 210 may include the inner opening ring 252 while excluding the outer adaptor ring 250. In such implementations, the inner opening ring 252 may include mating features 244 that are configured to interface with the elongate mating members 222 to form a secure connection therebetween. In some implementations, the elongate mating members 222 may be configured to be removably coupleable to the inner opening ring 252 (e.g., via the mating features 244) such that components of the wearable urinary collection apparatus 200 may be cleaned and/or replaced.

For example, in the implementation shown in FIG. 19A, the inner opening ring 252 includes one or more apertures 244a that are configured to receive the elongate mating members 222 (e.g., the loops 254 of the elongate mating members 222 shown in FIG. 18) to secure the elongate mating members 222 to the urine collection receptacle 210. For example, the inner opening ring 252 may be substantially cylindrical and may include two of the apertures 244a on opposing ends of the inner opening ring 252. The apertures 244a may extend through the inner opening ring 252 from an inboard side to an outboard side thereof. As described previously, the redundant urine collection area 216 may be formed by folding the upper end of the urine collection receptacle 210 inward over the inner opening ring 252 such that the inner opening ring 252 is disposed below the inversion 218. Accordingly, the urine collection receptacle 210 may include complementary apertures located adjacent to the one or more apertures 244a such that the elongate mating members 222 are passable through the one or more apertures 244a.

As another example, in the implementation shown in FIG. 19B, the inner opening ring 252 includes one or more slots 244b that, similarly to the apertures 244a, are configured to receive the elongate members 222 (e.g., the loops 254 of the elongate mating members 222 shown in FIG. 18) to secure the elongate mating members 222 to the urine collection receptacle 210. For example, the inner opening ring 252 may comprise a thin tubular ring portion and tabular portions extending upward therefrom (e.g., away from the lower end of the urine collection receptacle 210), and the one or more slots 244b may extend through the tabular portions. For example, in the illustrated implementation, the inner opening ring 252 includes the thin tubular ring portion extending around a circumference of the redundant urine collection area 216 to support the opening of the redundant urine collection area 216, and includes two of the tabular portions extending upwards from the thin tubular ring portion on opposing ends thereof. Furthermore, as shown, the inner opening ring 252 includes two of the slots 244b that each extend through a respective one of the tabular portions (e.g., that each extend from an inboard side to an outboard side of a respective one of the tabular portions). By spacing the one or more slots 244b away from the inversion 218, the elongate members 222 may be inserted through the one or more slots 244b without interference with the urine collection receptacle 210. In some implementations, rather than the one or more slots 244b that extend through respective tab portions, the inner opening ring 252 may include loops of material (not expressly shown) that extend therefrom and through which the elongate members 222 may extend. For example, the inner opening ring 252 may include two loops that extend upward from the inversion 218 at opposing ends of the inner opening ring 252. As another example, the inner opening ring 252 may include two loops that extend outward from outboard sides of opposing ends of the inner opening ring 252.

Figure 20:
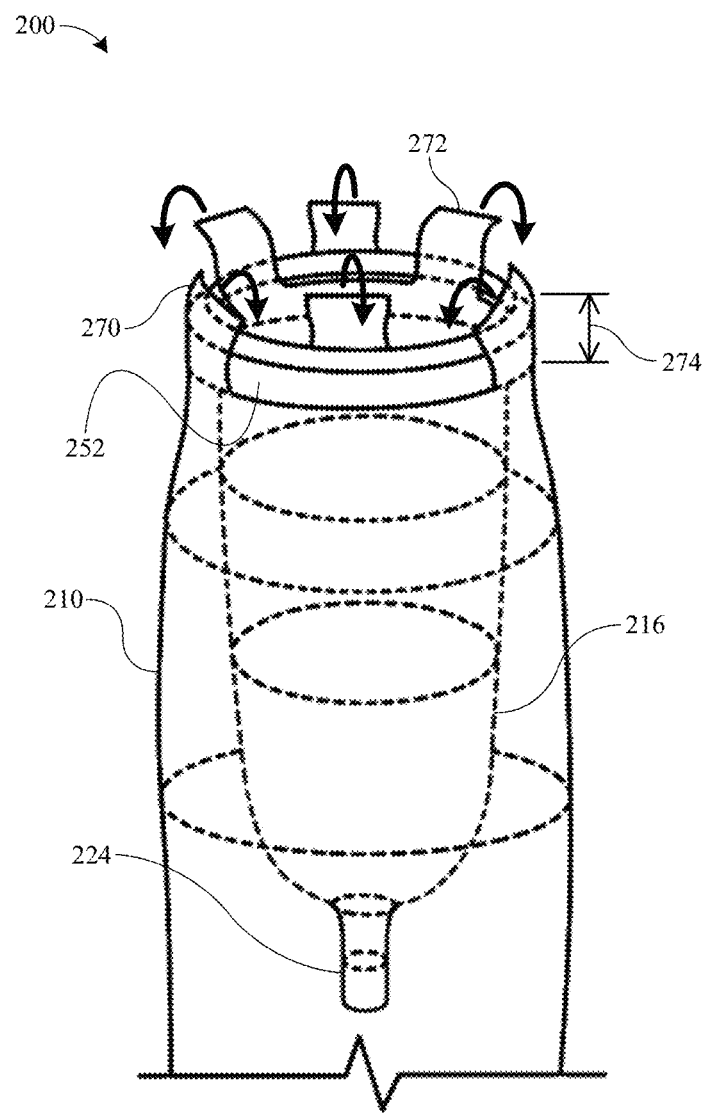
FIG. 20 is an upper perspective view illustration of another example of the urine collection receptacle of FIG. 15 demonstrating an example of a method for connecting examples of the urine collection receptacle and the redundant collection area to an example of the inner opening ring of FIG. 18, in which certain components are shown as hidden or transparent, indicated by broken lines, for clarity.

FIG. 20 is an upper perspective view illustration of another example the wearable urinary collection apparatus 200. In some implementations, the redundant urine collection area 216 may not be formed from the urine collection receptacle 210 but rather may be a separate components. In such an implementation, each of the urine collection receptacle 210 and the redundant urine collection area 216 may be connectable to the inner opening ring 252. For example, one or more of the urine collection receptacle 210 or the redundant urine collection area 216 may be connected to the inner opening ring 252 via adhesives or the like. In some implementations, such as where the urine collection receptacle 210 and/or the redundant urine collection area 216 are formed from TPU membrane, one or more of the urine collection receptacle 210 or the redundant urine collection area 216 may be connected to the inner opening ring 252 by laminating the urine collection receptacle 210 and/or the redundant urine collection area 216 directly to the inner opening ring 252. As shown, in the illustrated implementation as well as all other implementations described herein, the inner opening ring 252 may have a depth of about 2 cm.

As shown, to facilitate a connection with the inner opening ring 252, the urine collection receptacle 210 may include first strips 270 that extend upward from an upper terminal edge of thereof. Similarly, to facilitate a connection with the inner opening ring 252, the redundant urine collection area 216 may include second strips 272 that extend upward from an upper terminal edge thereof. Each of the first strips 270 and the second strips 272 may be configured to fold over the inner opening ring 252 to secure the urine collection receptacle 210 and the redundant urine collection area 216 to the inner opening ring 252, respectively. For example, as depicted in FIG. 20 by bolded arrows, the first strips 270 of the urine collection receptacle 210 may be configured to extend upward along an outboard side of the inner opening ring 252 and fold inward over the inner opening ring 252 to secure the urine collection receptacle 210 to the inner opening ring 252. Furthermore, also as depicted in FIG. 20 by bolded arrows, the second strips 272 of the redundant urine collection area 216 may be configured to extend upward along an inboard side of the inner opening ring 252 and fold outward over the inner opening ring 252 to secure the redundant urine collection area 216 to the inner opening ring 252. In some implementations, the first strips 270 and/or the second strips 272 may be secured to the inner opening ring 252 via an adhesive or may be laminated directly to the inner opening ring 252.

In some implementations of the wearable urinary collection apparatus shown in FIG. 20, the inner opening ring 252 may be excluded, and the redundant urine collection area 216 may be connected directly to the urine collection receptacle 210. For example, a circumference of an upper end of the redundant urine collection area 216 may be connected directly to a circumference of an upper end of the urine collection receptacle 210 that is complementary to the upper end of the redundant urine collection area 216. For example, the circumference of the upper end of the redundant urine collection area 216 may be adhered and/or laminated directly to the circumference of the upper end of the urine collection receptacle 210 to form a seal therebetween. In such an implementation, the urine collection receptacle 210 may include the first strips 270, in which the first strips 270 are configured to extend along an outboard side of the urine collection receptacle 210 and fold inward over the upper end of the redundant urine collection area 216 to secure the urine collection receptacle 210 to the redundant urine collection area 216. In addition to, or in the alternative, the redundant urine collection area 216 may include the second strips 272, in which the second strips 272 are configured to extend along an inboard side of the urine collection receptacle 210 and fold outward over the upper end of the urine collection receptacle 210 to secure the redundant urine collection area 216 to the urine collection receptacle 210.

Figure 21A:
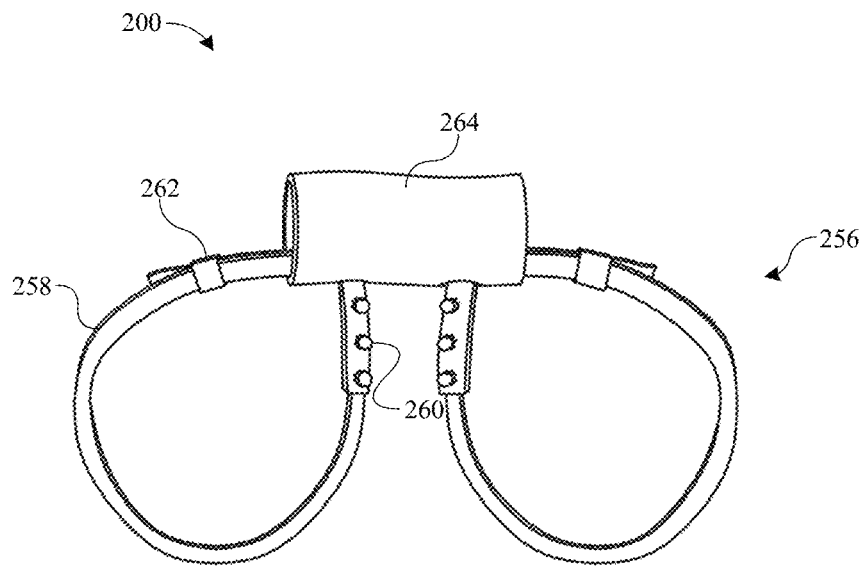
FIG. 21A is a perspective view illustration of an example of a harness according to the present disclosure including connecting feature for connection with the urine collection receptacle of FIG. 15.
Figure 21B:
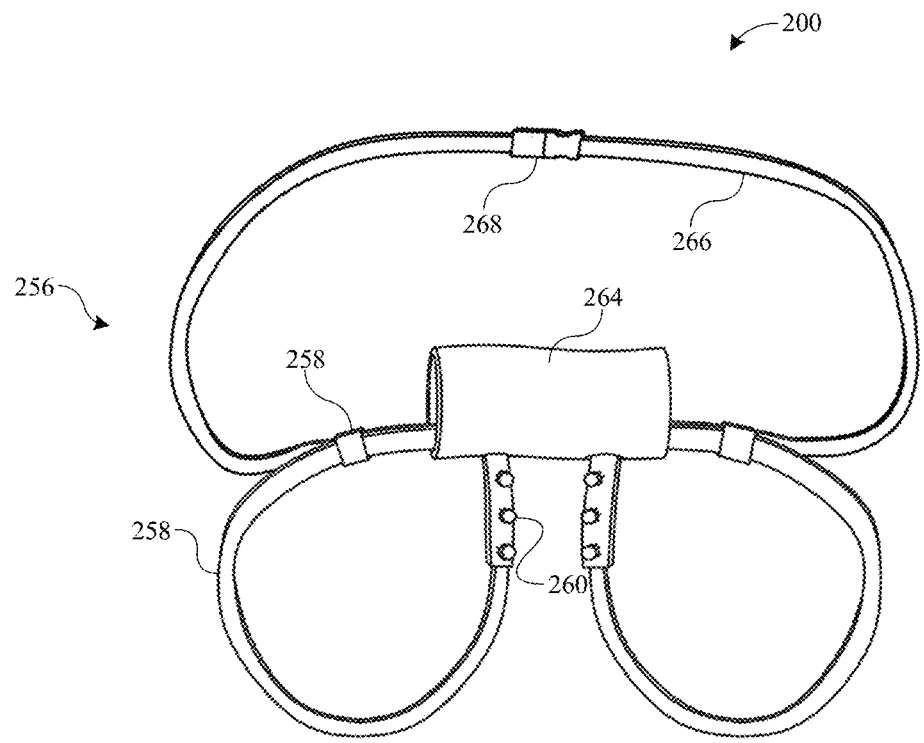
FIG. 21B is a perspective view illustration of another example of the harness of FIG. 18A including a waist strap.

FIGS. 21A-21B are upper perspective view illustrations of a harness 256 for the wearable urinary collection apparatus 200 according to an example. The harness 256 may be configured to support the urine collection receptacle 210 relative to a user. In some implementations, the harness 256 may be configured to support the urine collection receptacle 210 relative to a user such that the upper end (e.g., the inversion 218, the inner opening ring 252, and/or the outer adaptor ring 250) of the urine collection receptacle 210 is near, but spaced from the user (e.g., a pelvic area of the user), and the lower end of the urine collection receptacle 210 extends away from the user (e.g., downward). As explained in further detail below, the harness 256 may be configured to support the urine collection receptacle 210 relative to the user without loosening or slipping (e.g., when the user changes postures). For example, the harness 256 may be configured to support the urine collection receptacle 210 relative to the user without loosening or slipping (e.g., without substantial movement of the upper end of the urine collection receptacle 210 relative to the user) when the user moves from a seated position to a standing position and/or when the user moves from the standing position to the seated position. Furthermore, the harness 256 may be configured to support the urine collection receptacle 210 relative to the user such that the urine collection receptacle 210 clears (e.g., avoids interfering with) a seat (not shown) on which the user may sit. For example, the harness 256 may be configured to support the urine collection receptacle 210 relative to the user such that the urine collection receptacle 210 does not interfere with (e.g., contact) a toilet on which the user may sit. In such an implementation, for example, the harness 256 may support the urine collection receptacle 210 relative to the user such that the urine collection receptacle 210 is spaced inward (e.g., inside) or outwards (e.g., outside) of a bowl of the toilet.

In some implementations, the harness 256 may include securing straps 258 that extend around portions of the user to secure the harness 256 to the user. The securing straps 258 may extend from (e.g., through) either side of a padded member 264 and may be configured to extend around respective portions of the user, such as legs and/or the iliac crest of the buttocks, to support the urine collection receptacle 210 relative to the user. In some implementations, the securing straps 258 may further extend through apertures disposed on a bottom portion of the padded member 264 to form a loop that extends around the respective portions of the user. The apertures may be laterally spaced from each other to space the securing straps 258 outboard of the penis 202 of the user. The padded member 264 may be a cylindrical (e.g., rectangular when flat) component positioned centrally between the securing straps 258 such as to lay substantially across a lap of the user when the harness 256 is worn by the user. The padded member 264 may be configured to allow the harness 256 to sit comfortably against the user's body, typically in the lower abdominal or pelvic area, when the urine collection receptacle 210 is connected to the harness 256.

In some implementations, the harness 256 may include a waist strap 266 that passes through the padded member 264 and forms a loop configured to extend around a waist of the user. A fastening mechanism 268 may be positioned along the waist strap 266 to releasably connect opposing ends thereof. The waist strap 266 may be configured to further support the urine collection receptacle 210 relative to the user, for example, where the user is large and/or obese. Adjustment mechanisms 262 may be provided on the securing straps 258 to allow for size adjustment. The harness 256 may include complementary mating features 260 arranged vertically along strips extending downward from the padded member 264 for coupling the urine collection receptacle 210 to the harness 256 (e.g., for connection with the mating features of the elongate mating members 222. In some implementations, the strips may be connected to the padded member 264. In other implementations, however, the strips may extend along (e.g., may be formed along) the securing straps 258 (e.g., portions of respective ones of the securing straps 258 proximate the groin and/or pelvic area of the user). Accordingly, in some implementations, the complementary mating features 260 of the harness 256 may extend along portions of the securing straps 258 (e.g., portions of the securing straps 258 proximate the groin and/or pelvic area of the user). In some implementations, the complementary mating features 260 may comprise Velcro, small loops or hooks, pegs, snaps, or the like. The complementary mating features 260 may be removably couplable to the mating features of the urine collection receptacle 210 to removably connect the urine collection receptacle 210 to the harness 256. In some implementations, the waist strap 266 may extend through the padded member 264 and work in conjunction with the securing straps 258 to provide support for the wearable urinary collection apparatus 200. Furthermore, the harness 256 may work in conjunction with other components of the wearable urinary collection apparatus 200, such as the elongate cord 240, to provide a comprehensive solution for urinary collection and support.

Figure 22:
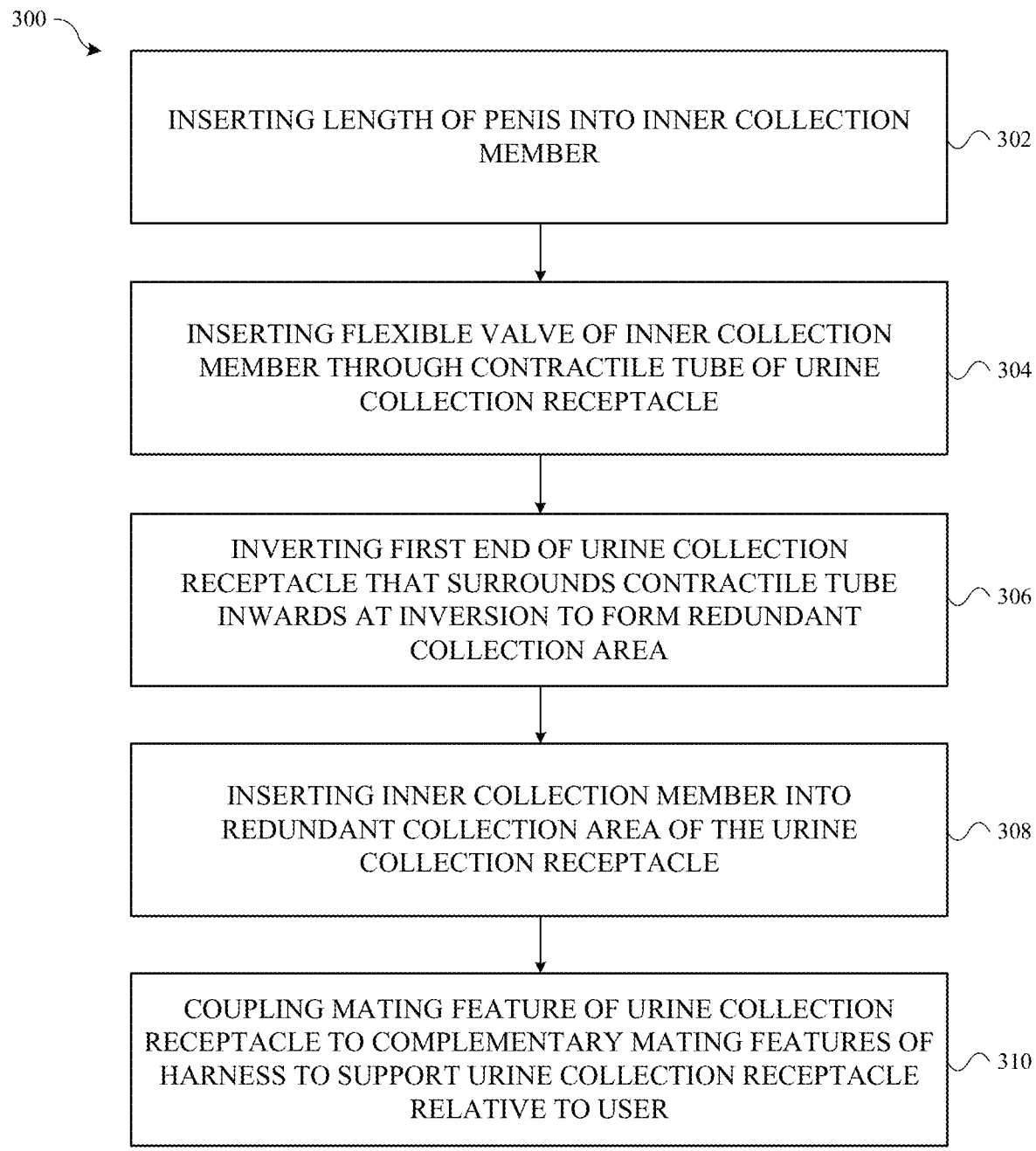
FIG. 22 is a flow diagram of an example of a method for affixing the wearable urinary collection apparatus of FIG. 15 to a user having a penis.

FIG. 22 illustrates a method 300 for affixing the wearable urinary collection apparatus 200 to a user having a penis 202. The method 300 may include several steps for assembling and using the wearable urinary collection apparatus 200.

The method may include inserting the penis 202 of the user into the inner collection member 212. In some implementations, the penile sleeve 230 of the inner collection member 212 may be unrolled over the shaft of the penis 202, similar to the application of a condom. This action helps to create a secure seal and prevents leakage at the base of the penis. The voiding area 232 should be positioned adjacent to the penis glans 206, aligning with the urethral opening 208 with the tubular port 224 to efficiently capture the urinary fluid 214 as it is voided.

The length of penis 202 inserted into the inner collection member 212 may vary depending on the individual user's anatomy and comfort level. However, it is generally recommended to insert enough length to ensure that the stream guide tube 234 is properly positioned relative to the urethral opening 208. This positioning is critical for directing urine flow into the urine collection receptacle 210 and minimizing the risk of leakage or backflow.

The method 300 may also include inserting 304 the one-way valve 236 of the inner collection member 212 through the tubular port 224 (e.g., the contractile stem tube 226) of the urine collection receptacle 210. In some implementations, inserting 304 the one-way valve 236 through the contractile stem tube 226 may form a constriction along the stream guide tube 234. The one-way valve 236 may be disposed within the urine collection receptacle 210 after insertion through the contractile stem tube 226.

In some implementations, inserting 304 the one-way valve 236 of the inner collection member 212 through the contractile stem tube 226 of the urine collection receptacle 210 may further comprise deforming the one-way valve 236 to reduce an axial size of the one-way valve 236 such that the one-way valve 236 is insertable through the contractile stem tube 226.

This step in the assembly process highlights an important consideration when inserting the one-way valve 236 through the contractile stem tube 226. The one-way valve 236, being a flexible component, may need to be temporarily deformed or compressed to facilitate its passage through the contractile stem tube 226. This deformation may involve reducing the cross-sectional size (e.g., an outer diameter) of the one-way valve 236, which may be achieved by gently folding or compressing the one-way valve 236.

The formation of a constriction along the stream guide tube 234 during this insertion serves as an additional safeguard against backflow. The contractile nature of the contractile stem tube 226 and/or the contractile stem tube 226 allows one or both of these components to grip the stream guide tube 234 tightly, creating a dynamic seal that may adapt to changes in pressure or movement. Once inserted, the one-way valve 236 is positioned within the urine collection receptacle 210. This placement ensures that any urine that passes through the valve is contained within the main body of the receptacle, further minimizing the risk of leakage or backflow. The positioning of the valve inside the receptacle also protects it from external forces that might compromise its function.

The method 300 may also include inverting 306 the upper end of the urine collection receptacle 210 that surrounds the contractile stem tube 226 inwards at the inversion 218 to form the redundant urine collection area 216. In some implementations, the urine collection receptacle 210 may extend longitudinally from a lower end to terminate at the inversion 218. The inverting action may involve folding the upper end of the urine collection receptacle 210 inward at a specific point, such as the inversion 218 or the inner opening ring 252. This creates a double-walled section at the upper portion of the receptacle, which serves multiple purposes as described previously.

The method 300 may also include inserting 308 the inner collection member 212 into the redundant urine collection area 216 of the urine collection receptacle 210. Inserting the inner collection member 212 into the redundant urine collection area 216 of the urine collection receptacle 210 establishes the primary interface between the user's anatomy and the urine collection receptacle 210. The inclusion of the contractile stem tube 226 within the redundant urine collection area 216 is an important feature of the configuration. As the inner collection member 212 is inserted, its stream guide tube 234 passes through the contractile stem tube 226. This creates a secure pathway for urine to flow from the user into the main body of the urine collection receptacle 210.

The redundant urine collection area 216 also accommodates any minor leaks that might occur at the interface between the stream guide tube 234 and the contractile stem tube 226. This fail-safe feature further enhances the reliability of the wearable urinary collection apparatus 200, ensuring that any potential leaks are contained within the system rather than reaching the user or their clothing.

The method 300 may also include coupling 310 mating features extending from the urine collection receptacle 210 to the complementary mating features 260 disposed along securing straps 258 of the harness 256. The placement of the complementary mating features 260 along the securing straps 258 provides flexibility in positioning the urine collection receptacle 210 relative to the user (e.g., to increase or decrease the spacing between the inversion 218 and the user).

This method 300 may provide a systematic approach to assembling and affixing the wearable urinary collection apparatus 200, ensuring proper alignment and connection of all components. The steps of the method 300 may be configured to maximize the effectiveness of the backflow prevention mechanisms and to ensure a secure and comfortable fit for the user.

While the exemplary implementations of the present disclosure have been described in detail, those familiar with the art will recognize various alternative configurations and implementations within the scope of the following claims. While various implementations may have been described as providing advantages or being preferred over other implementations with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The implementations discussed herein that are described as less desirable than other implementations or prior art implementations with respect to one or more characteristics are not outside the scope of the disclosure and may be desirable for particular applications. For example, while the several exemplary implementations of the urinary collection receptacle discussed herein are all discussed as being formed of thin, flexible plastic film/sheet material and perhaps also including support rings formed of rigid or semi-rigid materials, the present disclosure is not limited thereto.

What is claimed is:

1. A wearable urinary collection apparatus, comprising:
    an inner collection member configured to receive at least a portion of a length of a penis of a user, the inner collection member extending from an upper end to a lower end, the inner collection member comprising:
        a voiding area disposed at the lower end of the inner collection member; and
        a guide tube extending from the voiding area away from the upper end;
    a urine collection receptacle configured to collect urinary fluid therein, the urine collection receptacle comprising:
        one or more mating features;
        a redundant urine collection area configured to receive the inner collection member; and
        a tubular port disposed in the redundant urine collection area; and
    a harness configured to support the urine collection receptacle relative to the user, the harness comprising:
        securing straps configured to extend around respective portions of the user; and
        one or more complementary mating features extending along a portion of at least one of the securing straps, the one or more complementary mating features couplable to the one or more mating features of the urine collection receptacle,
    wherein when the inner collection member is received in the redundant urine collection area of the urine collection receptacle, the guide tube extends through the tubular port into the urine collection receptacle to define a fluid flow path from the inner collection member to the urine collection receptacle.

2. The wearable urinary collection apparatus of claim 1, further comprising:
    a contractile tube disposed within the tubular port of the urine collection receptacle,
    wherein when the inner collection member is received in the redundant urine collection area of the urine collection receptacle, the contractile tube constricts the guide tube to inhibit the urinary fluid collected in the urine collection receptacle from backflowing through the guide tube.

3. The wearable urinary collection apparatus of claim 2, wherein the guide tube comprises:
    a valve disposed at an end of the guide tube opposite the voiding area of the inner collection member,
    wherein the valve is configured to inhibit the urinary fluid collected in the urine collection receptacle from backflowing through the guide tube.

4. The wearable urinary collection apparatus of claim 2, wherein when the inner collection member is received in the redundant urine collection area of the urine collection receptacle, the redundant urine collection area is configured to collect the urinary fluid that leaks through an interface between the contractile tube and the guide tube.

5. The wearable urinary collection apparatus of claim 4, wherein when the inner collection member is received in the redundant urine collection area of the urine collection receptacle, the interface between the contractile tube and the guide tube cooperatively seals the urine collection receptacle to inhibit the urinary fluid collected in the urine collection receptacle from traveling to the redundant urine collection area.

6. The wearable urinary collection apparatus of claim 1, wherein the redundant urine collection area is formed from the upper end of the urine collection receptacle inverting inwards such that the tubular port and the upper end of the urine collection receptacle surrounding the tubular port is disposed within the urine collection receptacle.

7. The wearable urinary collection apparatus of claim 6, wherein the upper end of urine collection receptacle is tapered such that a diameter of the urine collection receptacle surrounding the tubular port at the upper end is smaller than a diameter of the urine collection receptacle at an intermediate portion of the urine collection receptacle.

8. The wearable urinary collection apparatus of claim 6, wherein the urine collection receptacle further comprises:
    an elastomeric ring disposed around a circumference of the urine collection receptacle,
    wherein the redundant urine collection area is formed from the upper end of the urine collection receptacle inverting inwards over the elastomeric ring such that the urine collection receptacle extends longitudinally from the lower end to terminate at the elastomeric ring.

9. The wearable urinary collection apparatus of claim 1, wherein the harness is configured to support the urine collection receptacle relative to the user such that the redundant urine collection area of the urine collection receptacle is spaced from the user and the lower end of the urine collection receptacle extends away from the user.

10. A urinary collection system, comprising:
an inner member configured to extend around at least a portion of a penis, the inner member comprising a guide tube extending from an end portion of the inner member; and
a membrane configured to collect urinary fluid therein, the membrane comprising a redundant fluid collection portion configured to extend around at least a portion of the inner member, the redundant fluid collection portion including a port,
wherein the guide tube of the inner member is configured to extend through the port of the membrane to seal the membrane at an interface between the guide tube and the port and to form a fluid flow path from the inner member into the membrane, and
wherein the redundant fluid collection portion is configured to collect the urinary fluid that leaks through the seal formed at the interface between the guide tube and the port.

11. The urinary collection system of claim 10, wherein the end portion of the inner member is configured to extend around a penis glans of the penis, and wherein the guide tube extends from the end portion of the inner member at a terminal end of the inner member.

12. The urinary collection system of claim 11, wherein the inner member further comprises a sleeve portion that extends from the end portion of the inner member and is configured to extend over a shaft of the penis.

13. The urinary collection system of claim 10, wherein the membrane comprises a tubular membrane that includes an upper end to a lower end, and wherein the redundant fluid collection portion is formed from the upper end of the tubular membrane inverting inwards at an inversion such that the tubular membrane extends longitudinally from the lower end to terminate at the inversion.

14. The urinary collection system of claim 10, wherein the port of the redundant fluid collection portion comprises a contractile member, and wherein the guide tube of the inner member is configured to extend through the contractile member to form a constriction along the guide tube that is configured to inhibit the urinary fluid from flowing from within the membrane through the guide tube to the inner member.

15. The urinary collection system of claim 14, wherein the inner member further comprises a one-way valve disposed along the guide tube, wherein the one-way valve is configured to be disposed within the membrane when the guide tube extends through the port of the membrane.

16. A method for affixing a wearable urinary collection apparatus to a user having a penis, the method comprising:
inserting a length of the penis into an inner collection member, the inner collection member including:
a penile sleeve configured to extend along a shaft of the penis; and
a stream tube configured to be adjacent to a terminal end of the penis, the stream tube including a flexible valve disposed at a terminal end thereof; and
inserting the flexible valve of the inner collection member through a contractile tube of a urine collection receptacle to dispose the flexible valve within the urine collection receptacle and to form a fluid flow path from the inner collection member into the urine collection receptacle, wherein the urine collection receptacle is configured to collect urine therein, and wherein an interface between the stream tube and the contractile tube is configured to seal the urine collection receptacle; and
inserting the inner collection member into a redundant collection area of the urine collection receptacle, wherein the redundant collection area is configured to collect the urine that leaks through the interface between the stream tube and the contractile tube, and wherein the redundant collection area includes the contractile tube.

17. The method of claim 16, further comprising:
inverting an upper end of the urine collection receptacle that surrounds the contractile tube inwards at an inversion to form the redundant collection area, wherein the urine collection receptacle extends longitudinally from a lower end of the urine collection receptacle to terminate at the inversion.

18. The method of claim 16, further comprising:
coupling mating features extending from the urine collection receptacle to complementary mating features disposed along securing straps of a harness, wherein the securing straps are configured to extend around respective portions of the user to support the urine collection receptacle relative to the user.

19. The method of claim 16, wherein inserting the flexible valve of the inner collection member through the contractile tube of the urine collection receptacle forms a constriction along the stream tube that inhibits the fluid flow path from the urine collection receptacle to the inner collection member.

20. The method of claim 16, wherein inserting the flexible valve of the inner collection member through the contractile tube of the urine collection receptacle further comprises:
deforming the flexible valve to reduce an axial size of the flexible valve such that the flexible valve is insertable through the contractile tube.

\* \* \* \* \*